United States Patent [19]

Edmunds et al.

[11] Patent Number: 5,200,411
[45] Date of Patent: Apr. 6, 1993

[54] HETEROATOMS-CONTAINING TRICYCLIC COMPOUNDS

[75] Inventors: Andrew J. F. Edmunds; Maximilian Grassberger, both of Vienna, Austria

[73] Assignee: Sandoz, Ltd., Basel, Switzerland

[21] Appl. No.: 710,348

[22] Filed: Jun. 13, 1991

Related U.S. Application Data

[63] Continuation-in-part of Ser. No. 656,046, Feb. 14, 1991, abandoned.

[30] Foreign Application Priority Data

Jun. 14, 1989 [DE] Fed. Rep. of Germany ....... 3919466
Oct. 20, 1989 [DE] Fed. Rep. of Germany ....... 3934991

[51] Int. Cl.$^5$ .................. C07D 491/16; A61K 31/395
[52] U.S. Cl. ...................................... 514/291; 514/63; 540/452; 540/456
[58] Field of Search ................. 540/456, 452; 514/291, 514/63

[56] References Cited

FOREIGN PATENT DOCUMENTS

| | | |
|---|---|---|
| 0323865 | 7/1989 | European Pat. Off. ............ 540/456 |
| 0349049 | 1/1990 | European Pat. Off. ............ 540/456 |
| 0349061 | 1/1990 | European Pat. Off. ............ 540/456 |
| 0353678 | 2/1990 | European Pat. Off. ............ 540/456 |
| 0358508 | 3/1990 | European Pat. Off. ............ 540/456 |
| 0364031 | 4/1990 | European Pat. Off. ............ 540/456 |
| 0364032 | 4/1990 | European Pat. Off. ............ 540/456 |
| WO8905304 | 6/1989 | PCT Int'l Appl. ................. 540/456 |

Primary Examiner—Robert T. Bond
Attorney, Agent, or Firm—Gerald D. Sharkin; Robert S. Honor; Thomas O. McGovern

[57] ABSTRACT

The compounds of formula I

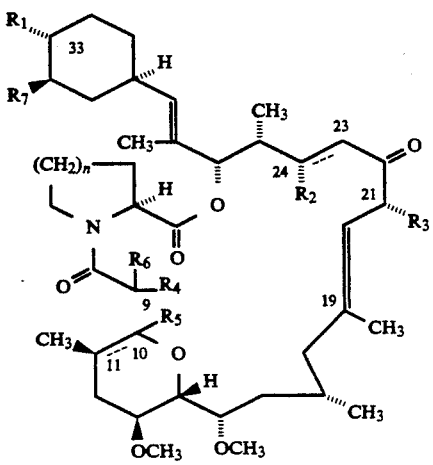

wherein the substituents have various significances, possess pharmacological, particularly antiinflammatory and immunosuppressant activity.

They can be prepared by one or more of the following process variants: reduction, deprotection, acylation, reaction with N,N'-carbonyl- or N,N'-thiocarbonyl-diimidazole, halogenation, splitting off of hydrogen halide, reaction with a hydrogen carbonate, radical deoxygenation, dehydration or reaction with diazomethane of -ethane, optionally under transient protection of reactive groups which it is not desired to react.

7 Claims, No Drawings

HETEROATOMS-CONTAINING TRICYCLIC COMPOUNDS

This application is a continuation in part of U.S. patent application, Ser. No. 07/656,046, filed Feb. 14, 1991 now abandoned.

The invention relates to the field of macrolides. It concerns the compounds of formula I

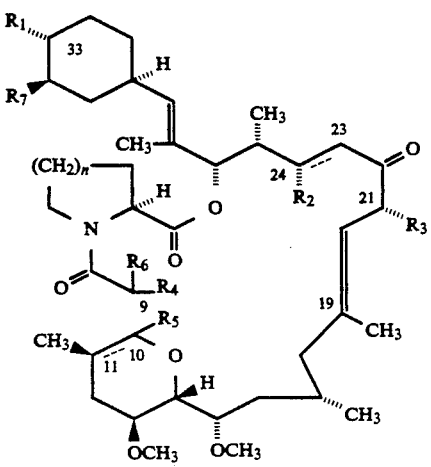

I wherein
$R_1$ is acyloxy or optionally protected hydroxy;
$R_2$ is optionally protected hydroxy or is absent, whereby, when $R_3$ is cyclopropylmethyl or methylcyclopropylmethyl, $R_2$ additionally can be hydrogen;
$R_3$ is methyl, ethyl, n-propyl, allyl, cyclopropylmethyl or methylcyclopropylmethyl;
either
$R_4$ is hydrogen, optionally protected hydroxy, acyloxy or is absent; and
$R_5$ is unprotected hydroxy, halogen of atomic number of from 9 to 53 or is absent; or
$R_4$ and $R_5$ together form a group —OC(=O)O— or —OC(=S)O—; and
$R_6$ is hydrogen or, when $R_4$ and $R_5$ together form a group —OC(=O)O—, is hydrogen or methoxy; or
$R_4$ and $R_6$ together form a group oxo; and
$R_5$ is unprotected hydroxy or halogen of atomic number of from 9 to 53 or is absent;
$R_7$ is unprotected hydroxy or methoxy; and
n is 1 or 2,
with the provisos that
a) at least one of $R_1$, $R_2$, $R_4$ and $R_5$ is other than unprotected hydroxy;
b) when $R_4$ and $R_6$ together form a group oxo, then either $R_3$ is cyclopropylmethyl or methylcyclopropylmethyl; or $R_5$ is halogen of atomic number of from 9 to 53 or is absent; and
c) when $R_1$ is acyloxy, then either $R_4$ and $R_6$ are other than together a group oxo; or $R_4$ and $R_6$ together form a group oxo and $R_5$ is halogen of atomic number of from 9 to 53 or is absent,
hereinafter referred to as "the compounds of the invention".

As is evident from formula I and the definition of the substituents
when $R_2$ is absent then one hydrogen atom in position 23 is also absent and there is a double bond in position 23,24 as indicated by the symbol of a dotted line;
when $R_4$ is absent then $R_5$ is also absent and there is a double bond in position 9,10 as indicated by the symbol of a dotted line;
when $R_5$ is absent then either $R_4$ is also absent and there is a double bond in position 9,10 as indicated by the symbol of a dotted line; or the hydrogen atom in position 11 is also absent and there is a double bond in position 10,11 as indicated by the symbol of a dotted line; but there can be no more than one double bond, either in position 9,10 or in position 10,11.

Formula I is meant to cover the compounds in free form and, where such forms may exist, in salt form.

In a subgroup of compounds of formula I
$R_1$ is acetoxy or optionally protected hydroxy;
$R_3$ is methyl, ethyl, n-propyl or allyl;
$R_4$ is hydrogen, optionally protected hydroxy or acetoxy and
$R_5$ is unprotected hydroxy, halogen of atomic number of from 9 to 53 or is absent; or
$R_4$ and $R_5$ together form a group —OC(=O)O— or —OC(=S)O—;
$R_7$ is methoxy; and
the remaining substituents are as defined above under formula I.

In a further subgroup of compounds of formula I
$R_1$ is acetoxy or optionally protected hydroxy;
$R_2$ is optionally protected hydroxy;
$R_3$ is cyclopropylmethyl or methylcyclopropylmethyl;
$R_4$ and $R_5$ are unprotected hydroxy;
$R_6$ is hydrogen;
$R_7$ is methoxy; and n is 2.

Further subgroups are compounds of formula I wherein the substituents have the following significances:
$R_1$: acetoxy, pivaloyloxy, isobutanoyloxy or optionally protected hydroxy; especially acetoxy, pivaloyloxy or unprotected hydroxy;
$R_2$: optionally protected hydroxy; especially unprotected hydroxy;
$R_3$: ethyl, allyl, cyclopropylmethyl or methylcyclopropylmethyl;
$R_4$: unprotected hydroxy, acetoxy or together with $R_6$ a group oxo; especially unprotected hydroxy;
$R_5$: unprotected hydroxy or halogen of atomic number of from 9 to 53; especially unprotected hydroxy; or
$R_4$ and $R_5$: together a group —OC(=O)O— or —OC(=S)O—; especially a group —OC(=O)O—;
$R_6$: hydrogen;
$R_7$: methoxy.

Preferably there is a single bond in position 9,10 and a single or a double bond in positions 10,11 and 23,24. More preferably there is a single bond in positions 9,10 and 23,24 and a single or a double bond in position 10,11.

$R_1$ preferably is acyloxy or unprotected hydroxy. $R_2$ preferably is optionally protected hydroxy, especially unprotected hydroxy. $R_3$ preferably is ethyl, allyl, cyclopropylmethyl or methylcyclopropylmethyl, especially ethyl or allyl. $R_4$ preferably is hydrogen, unprotected hydroxy or together with $R_5$ a group —OC(=O)O— or together with $R_6$ a group oxo. $R_7$ preferably is methoxy. n preferably is 2.

Acyloxy preferably is alkylcarbonyloxy of altogether 2 to 8 carbon atoms, preferably of altogether 2 to 6 carbon atoms, particularly 2 to 5 carbon atoms, such as acetoxy, pivaloyloxy or isobutanoyloxy; or benzoyloxy optionally substituted by halogen of atomic number of from 9 to 53, preferably monosubstituted, preferably by chlorine, preferably in 4 position; it especially is acetoxy, pivaloyloxy or 4-chlorobenzoyloxy, especially acetoxy or pivaloyloxy.

Protected hydroxy preferably is hydroxy protected by a silicon-containing group, it is e.g. tert-butyldimethylsilyloxy.

Halogen of atomic number of from 9 to 53 preferably is of atomic number of from 9 to 35; it preferably is chlorine or bromine, especially chlorine.

A further subgroup of compounds of formula I is the compounds of formula I wherein $R_1$ is acetoxy or optionally protected hydroxy;
$R_2$ is optionally protected hydroxy or is absent;
$R_3$ is methyl, ethyl, n-propyl or allyl; either
$R_4$ is hydrogen, optionally protected hydroxy, acetoxy or is absent; and
$R_5$ is unprotected hydroxy or halogen of atomic number of from 9 to 53 or is absent; or
$R_4$ and $R_5$ together form a group —OC(=O)O— or —OC(=S)O—; and
$R_6$ is hydrogen or, when $R_4$ and $R_5$ together form a group —OC(=O)O—, is hydrogen or methoxy; or
$R_4$ and $R_6$ together form a group oxo; and
$R_5$ is unprotected hydroxy or halogen of atomic number of from 9 to 53 or is absent;
$R_7$ is methoxy; and
n is 1 or 2,
with the provisos that
a) at least one of $R_1$, $R_2$, $R_4$ and $R_5$ is other than unprotected hydroxy;
b) when $R_4$ and $R_5$ together form a group oxo, then $R_5$ is halogen of atomic number of from 9 to 53 or is absent; and
c) when $R_1$ is acetoxy, then either $R_4$ and $R_6$ are other than together a group oxo; or $R_4$ and $R_6$ together form a group oxo and $R_5$ is halogen of atomic number of from 9 to 53 or is absent, i.e. the compounds herewith defined as compounds $Ip_1$.

A further subgroup of compounds of formula I is the compounds of formula I wherein $R_1$ is acetoxy or optionally protected hydroxy;
$R_2$ is hydrogen or optionally protected hydroxy;
$R_3$ is cyclopropylmethyl or methylcyclopropylmethyl; either
$R_4$ and $R_5$ are unprotected hydroxy; and
$R_6$ is hydrogen; or
$R_4$ and $R_6$ together form a group oxo; and
$R_5$ is unprotected hydroxy;
$R_7$ is methoxy; and
n is 2,
with the provisos that
a) at least one of $R_1$, $R_2$, $R_4$ and $R_5$ is other than unprotected hydroxy;
b) when $R_1$ is acetoxy, then $R_4$ and $R_5$ are other than together a group oxo;

i.e. the compounds herewith defined as compounds $Ip_2$.

A further subgroup of compounds of formula I is the compounds of formula I wherein $R_1$ is alkylcarbonyloxy of altogether 2 to 6 carbon atoms, benzoyloxy monosubstituted by halogen of atomic number of from 9 to 53 or hydroxy optionally protected by tert-butyldimethylsilyl;
$R_2$ is hydroxy optionally protected by tert-butyldimethylsilyl or is absent;
$R_3$ is ethyl, allyl, cyclopropylmethyl or methylcyclopropylmethyl;
either
$R_4$ is hydrogen, unprotected hydroxy, acetoxy or is absent;
$R_5$ is unprotected hydroxy, halogen of atomic number of from 9 to 53 or is absent; or
$R_4$ and $R_5$ together form a group —OC(=O)O— or —OC(=S)O—; and
$R_6$ is hydrogen or, when $R_4$ and $R_5$ together form a group —OC(=O)O—, is hydrogen or methoxy; or
$R_4$ and $R_6$ together form a group oxo; and
$R_5$ is unprotected hydroxy, halogen of atomic number of from 9 to 53 or is absent;
$R_7$ is methoxy; and
n is 2,
with the provisos that
a) at least one of $R_1$, $R_2$, $R_4$ and $R_5$ is other than unprotected hydroxy;
b) when $R_4$ and $R_6$ together form a group oxo, then either $R_3$ is cyclopropylmethyl or methylcyclopropylmethyl; or $R_5$ is halogen of atomic number of from 9 to 53 or is absent; and
c) when $R_1$ is alkylcarbonyloxy or benzoyloxy as defined above for this subgroup of compounds, then either $R_4$ and $R_6$ are other than together a group oxo; or $R_4$ and $R_6$ together form a group oxo and $R_5$ is halogen of atomic number of from 9 to 53 or is absent, i.e. the compounds herewith defined as compounds Is. In a subgroup thereof halogen is of atomic number of from 9 to 35, especially chlorine.

A compound of formula I can be obtained by a process comprising a) for the preparation of a compound of formula I as defined above under formula I with the further proviso that $R_4$ is unprotected hydroxy and $R_6$ is hydrogen (i.e. a compound Ia), reducing a corresponding compound of formula I as defined above under formula I with the further proviso that $R_4$ and $R_6$ together form a group oxo (i.e. a compound Ib);

b) for the preparation of a compound of formula I as defined above under formula I with the further proviso that at least one of $R_1$, $R_2$ and $R_4$ is unprotected hydroxy (i.e. a compound Ic), deprotecting a corresponding compound of formula I as defined above under formula I with the further proviso that at least one of $R_1$, $R_2$ and $R_4$ is protected hydroxy (i.e. a compound Id);

c) for the preparation of a compound of formula I as defined above under formula I with the further proviso that at least one of $R_1$ and $R_4$ is acyloxy (i.e. a compound Ie), acylating a corresponding compound of formula I as defined above under formula I with the further proviso that at least one of $R_1$ and $R_4$ is unprotected hydroxy (i.e. a compound If);

d) for the preparation of a compound of formula I as defined above under formula I with the further proviso that $R_4$ and $R_5$ together form a group —OC(=O)O— or —OC(=S)O— and $R_6$ is hydrogen (i.e. a compound Ig), reacting with N,N'-carbonyl- or N,N'-thiocarbonyldiimidazol a corresponding compound of formula I as defined above under formula I with the further proviso that $R_4$ and $R_5$ are unprotected hydroxy and $R_6$ is hydrogen (i.e. a compound Ih);

e) for the preparation of a compound of formula I as defined above under formula I with the further proviso that $R_5$ is halogen of atomic number of from 9 to 53 (i.e. a compound Ii), halogenating a corresponding compound of formula I as defined above under formula I with the further proviso that $R_5$ is unprotected hydroxy (i.e. a compound Ij);

f) for the preparation of a compound of formula I as defined above under formula I with the further proviso that $R_5$ is absent and there is a double bond in position 10,11 (i.e. a compound Ik), splitting off hydrogen halide from a corresponding compound Ii;

g) for the preparation of a compound of formula I as defined above under formula I with the further proviso that $R_4$ and $R_5$ together form a group —OC(=O)O— and $R_6$ is methoxy (i.e. a compound Im), reacting with a hydrogen carbonate a corresponding compound of formula I as defined above under formula I with the further proviso that $R_4$ and $R_6$ together form a group oxo and $R_5$ is halogen of atomic number of from 9 to 53 (i.e. a compound In);

h) for the preparation of a compound of formula I as defined above under formula I with the further proviso that $R_4$ and $R_5$ are absent (i.e. a compound Io), reacting with tributyl tin hydride a corresponding compound of formula I as defined above under formula I with the further proviso that $R_4$ and $R_5$ together form a group —OC(=S)O— (i.e. a compound Ip);

i) for the preparation of a compound of formula I as defined above under formula I with the further proviso that $R_2$ and $R_5$ are absent and there is a double bond in positions 10,11 and 23,24 (i.e. a compound Iq), dehydrating a corresponding compound of formula I as defined above under formula I with the further proviso that $R_2$ and $R_5$ are unprotected hydroxy (i.e. a compound Ir); or j) for the preparation of a compound of formula I as defined above under formula I with the further proviso that $R_3$ is cyclopropylmethyl or methylcyclopropylmethyl and there is a single bond in position 9,10 (i.e. a compound Is), reacting with diazomethane or -ethane a corresponding compound of formula I as defined above under formula I with the further proviso that $R_3$ is allyl and there is a single bond in position 9,10 (i.e. a compound It), whereby in the above process variants reactive groups which are not meant to take part in a reaction may be transiently protected and the protecting group(s) split off after completion of the reaction.

The above process variants are effected in a manner analogous to known methods:

In process variant a) (reduction) the reducing agent is e.g. diisobutylaluminium hydride (DIBAH). The reaction preferably is effected in an inert solvent such as a cyclic ether, e.g. tetrahydrofurane. Preferably low temperatures, e.g. $-78°$ C. are used. The reaction can however also be effected e.g. with lithium aluminium hydride in e.g. tetrahydrofurane or with tetramethylammonium triacetoxyborohydride in e.g. acetonitrile/acetic acid. The configuration at the carbon atom in the 9 position (C-9) in the resultant product can be influenced by appropriate selection of the reduction method and reaction conditions. Normally a mixture of the (R)- and (S)-isomers is obtained, in unequal amounts. Thus when DIBAH in hexane is used, predominantly the (R)-isomer is obtained, whereas mainly the (S)-isomer is formed with LiAlH$_4$ or tetramethylammonium triacetoxyborohydride. The resultant isomeric mixture can be separated in known manner, e.g. chromatographically.

In process variant b) (deprotection) protecting groups such as silyl groups are split off e.g. using hydrofluoric acid in a solvent such as acetonitrile. The temperature preferably is about room temperature. The reaction conditions (temperature, duration, etc.) can be selected in such manner that all or only a part of the protecting groups are split off. Partial deprotection is of particular benefit where it is desired in a subsequent reaction step to react a specific hydroxy group. Deprotection may be accompanied by dehydration to compounds having a double bond in 10,11 position, particularly when $R_4$ is hydroxy with the (R)-configuration at C-9. When deprotection is effected on a compound having a double bond in 9,10 position, simultaneous rehydration may occur to give a compound wherein $R_4$ and $R_6$ are hydrogen and $R_5$ is hydroxy.

Process variant c) (acylation) is e.g. effected by reaction with an acyl anhydride such as acetanhydride in the presence of a base. Preferably an inert solvent such as pyridine is used, where indicated with an additive such as 4-dimethylaminopyridine. Depending upon which hydroxy groups are unprotected one or more hydroxy group(s) is (are) acylated.

Process variant d) (reaction with N,N'-carbonyl- or N,N'-thiocarbonyldiimidazole) preferably is effected in an inert solvent such as a chlorinated hydrocarbon, e.g. dichloromethane. The temperature preferably is room temperature. The imidazole preferably is added in portions.

Process variant e) (halogenation) preferably is effected in an inert solvent such as diethylether. The reagent preferably is a thionyl halide such as thionyl chloride.

Process variant f) (splitting off hydrogen halide) preferably is effected in an inert solvent such as a cyclic ether, e.g. tetrahydrofurane. Preferably about room temperature is used. The reagent is e.g. 1,8-diazabicyclo[5.4.0]undec-7-ene.

Process variant g) (reaction with a hydrogen carbonate) preferably is effected using an alcohol such as methanol as the solvent. The hydrogen carbonate is e.g. sodium hydrogen carbonate.

In process variant h) (radical deoxygenation) preferably a tin hydride, especially tributyl tin hydride is used, preferably in the presence of a radical starter such as azoisobutyronitrile. Preferably the reaction is effected in an inert solvent such as an aromatic hydrocarbon, e.g. toluene. Temperatures between room temperature and the boiling point of the solvent are preferred, especially between about 80° and about 110° C.

Process variant i) (dehydration) is e.g. effected by reaction with a sulfonic acid chloride such as methane sulfonic acid chloride, preferably in the presence of an organic base such as 4-dimethylaminopyridine. An inert solvent preferably is used, e.g. acetonitrile. The reaction is performed preferably at about room temperature.

In process variant j) (reaction with diazomethane or -ethane) an inert solvent such as an ether, e.g. diethylether, preferably is used. The temperature is e.g. from about 0° C. to about $-15°$ C. Preferably the reaction is effected in the presence of a catalyst such as palladium(II) acetate. The diazo compound preferably is dissolved in the same solvent as the solution of compound It and added thereto.

Protection and deprotection, working-up, isolation and purification may also be effected in accordance with known procedures. When $R_3$ is methylcyclopropylmethyl there is an additional center of asymmetry. The corresponding diastereoisomeric mixtures may be fractionated in conventional manner, e.g. chromatographically.

Insofar as their preparation is not specifically described herein, e.g. in the Examples, the compounds used as starting materials are known or can be obtained in conventional manner from known compounds, e.g. starting from appropriate Streptomyces strains such as *Streptomyces tsukubaensis* No. 9993 described in e.g. Fujisawa EP 184162. Samples can be obtained from the Fermentation Research Institute, Tsukuba, Ibaraki 305, Japan under the provisions of the Budapest Treaty under deposit No. FERM BP-927 or, since this strain has been redeposited on Apr. 27, 1989 e.g. as disclosed in Sandoz EP 356399, from the Agricultural Research Culture Collection International Depository, Peoria, Ill. 61604, USA under the provisions of the Budapest Treaty under deposit No. NRRL 18488.

The following Examples illustrate the invention and are not limitative. All temperatures are in degrees Centigrade. All NMR spectra are in CDCl$_3$. The abbreviations have the following meanings:

| | |
|---|---|
| acs: | amorphous colourless solid; |
| cf: | colourless foam; |
| cPropme: | cyclopropylmethyl; |
| db: | double bond; |
| Et: | ethyl |
| FK506: | the compound of formula |

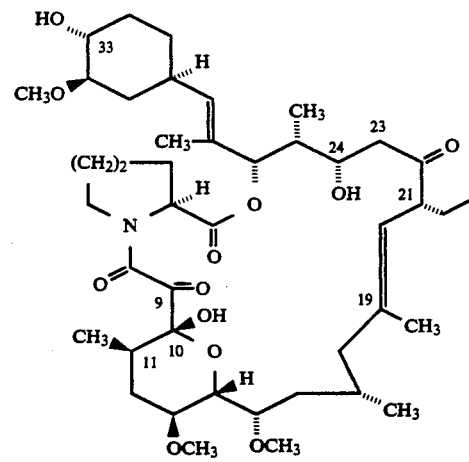

i.e. R$_1$, R$_2$ and R$_5$ = OH;
R$_3$ = allyl;
R$_4$ + R$_6$ = oxo;
R$_7$ = methoxy;
n = 2; and
there is a single bond in positions 9,10; 10,11; and 23,24;
excluded by proviso b);

i.e. 17α-allyl-1β,14α-dihydroxy-12-[2'-(4"(R)-hydroxy-3"(R)-methoxycyclohex-1"(R)-yl)-1'-methyl-trans-vinyl]-23α,25β-dimethoxy-13α,19,21α,27β-tetramethyl-11,28-dioxa-4-azatricyclo[22.3.1.0$^{4,9}$]octacos-18-trans-ene-2,3,10,16-tetraone
(according to the atom numbering in EP 184162);
FR520: the compound of formula

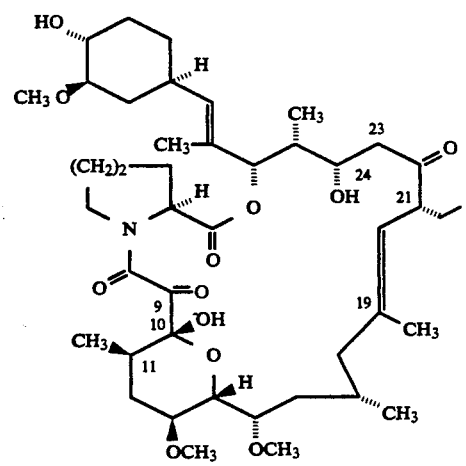

i.e. R$_1$, R$_2$ and R$_5$ = OH;
R$_3$ = ethyl;
R$_4$ + R$_6$ = oxo;
R$_7$ = methoxy;
n = 2; and
there is a single bond in positions 9,10; 10,11; and 23,24;
excluded by proviso b);

i.e. 17α-ethyl-1β,14α-dihydroxy-12-[2'-(4"(R)-hydroxy-3"(R)-methoxycyclohex-1"(R)-yl)-1'-methyl-trans-vinyl]-23α,25β-dimethoxy-13α,19,21α,27β-tetramethyl-11,28-dioxa-4-azatricyclo[22.3.1.0$^{4,9}$]octacos-18-trans-ene-2,3,10,16-tetraone
(according to the atom numbering in EP 184162);

| | |
|---|---|
| MecPropme: | methylcyclopropylmethyl; |
| OAc: | acetoxy; |
| OBzCl: | 4-chlorobenzoyloxy; |
| OEt: | ethoxy; |
| OiBu: | isobutanoyloxy; |
| OMe (or MeO): | methoxy; |
| OPiv: | pivaloyloxy; |
| OtBDMS: | tert-butyldimethylsilyloxy; |
| sb: | single bond. |

EXAMPLE 1

24,33-Bis-(tert-butyldimethylsilyloxy)-9(R)-dihydro-FK506

Formula I: R$_1$,R$_2$=OtBDMS; R$_3$=allyl; R$_4$=OH, (R)-configuration at C-9; R$_5$=OH; R$_6$=H; R$_7$=MeO; n=2; single bonds in positions 9,10; 10,11; and 23,24

Process variant a), reduction 1 g 24,33-bis-(tert-butyldimethylsilyloxy)-FK506 is dissolved in 20 ml of dry tetrahydrofurane and the solution cooled to −78°. 5 ml of a 20% solution of diisobutylaluminium hydride in hexane are added under stirring. After 1.5 hour stirring at that temperature the excess reagent is destroyed with 0.1N hydrochloric acid solution and the precipitate filtered off. The organic phase is diluted with ethyl acetate, washed thrice with water and dried over sodium sulfate. The solvent is evaporated under reduced pressure and the resultant crude product purified by column chromatography over silicagel using acetic acid ethyl ester as the eluant. The title compound is obtained (colourless foam):

$^1$H-NMR: 2.53 and 2.38 (dd, J$_1$=6, J$_2$=17 Hz and dd, J$_1$=1, J$_2$=17 Hz, H-23); 2.96 (ddd, J$_1$=5, J$_2$=8, J$_3$=11 Hz, H-32); 3.79 (dd, J$_1$=2, J$_2$=8 Hz, H-14); 4.28 (m, H-24); 4.39 (d, J=12 Hz, H-9); 4.83 (m, H-2); 5.19 (s, broad, H-26);

$^{13}$C-NMR: 69.8 (C-9); 98.0 (C-10); 115.9 (C-38); 121.9 (C-20); 128.5 (C-29); 132.8 (C-28); 136.4 (C-37); 139.4 (C-19); 168.7 (C-1); 173.5 (C-8); 210.7 (C-22).

The starting material is obtained as follows: 20 g FK506 are dissolved in 400 ml of dry dimethylformamide, 5.08 g imidazole and 11.25 g tert-butyldimethylchlorosilane are added in portions and the mixture is stirred for 110 hours at room temperature. The reaction mixture is diluted with acetic acid ethyl ester and washed five times with water. The organic phase is dried over sodium sulfate and the solvent distilled off under reduced pressure. The resultant crude product is purified by chromatography over silicagel using hexane/acetic acid ethyl ester 3:1 as the eluant. 24,33-Bis-(tert-butyldimethylsilyloxy)-FK506 is obtained.

EXAMPLE 2

24,33-Bis-(tert-butyldimethylsilyloxy)-9(S)-dihydro-FK506

Formula I: $R_1, R_2, R_3, R_5, R_6, R_7$, n and bonds in positions 9,10; 10,11; and 23,24: as for Example 1; $R_4$=OH, (S)-configuration at C-9

Process variant a), reduction

Method 1: To a solution of 1 g 24,33-bis-(tert-butyldimethylsilyloxy)-FK506 in 8 ml of dry tetrahydrofuran is added under stirring at 0° 0.1 g lithium aluminium hydride in portions. The mixture is allowed to reach room temperature and stirred for two more hours. The reaction mixture is successively reacted with acetic acid ethyl ester and saturated ammonium chloride solution, the organic phase is separated and the aqueous phase extracted thrice with acetic acid ethyl ester. The combined organic phases are washed thrice with water, dried over sodium sulfate and the solvent is distilled off under reduced pressure. The product is purified by column chromatography over silicagel using a mixture of dichloromethane/methanol 30:1 as the eluant. The title compound is obtained as a colourless foam;

Method 2: 10.1 g 24,33-bis-(tert-butyldimethylsilyloxy)-FK506 are added in portions under stirring at −20° to a solution of 7.9 g tetramethylammoniumtriacetoxyborohydride in 60 ml of acetonitrile and 60 ml of acetic acid. The reaction mixture is brought to 0° to 6° and stirred for 4 hours at that temperature. 10 ml of water are added and agitation continued for 10 minutes. The mixture is extracted thrice with dichloromethane, the organic phase is washed once with water and twice with saturated sodium chloride solution, dried over magnesium sulfate and the solvent evaporated under reduced pressure. The resultant crude product is purified by column chromatography over silicagel using toluene/acetic acid ethyl ester 4:1 to 2:1 as the eluant. The title compound is obtained as a colourless foam:

$^1$H-NMR: 4.46 (d, J=10 Hz, H-9);
$^{13}$C-NMR: 68.5 and 71.2 (C-9 and C-24); 99.5 (C-10); 115.8 (C-38); 122.3 (C-20); 130.8 (C-29); 132.9 (C-28); 136.1 (C-37); 140.3 (C-19); 169.6 (C-1); 173.3 (C-8); 209.5 (C-22).

EXAMPLE 3

24,33-Bis-(tert-butyldimethylsilyloxy)-9(S)-dihydro-10-desoxy-$\Delta^{10,11}$-FK506 and the corresponding 9(R) isomer Formula I: $R_1, R_2, R_3, R_4, R_6, R_7$, n and bonds in positions 9,10 and 23,24: as for Example 1; $R_5$ absent; double bond in position 10,11; (S)- and, respectively, (R)-configuration at C-9

Process variant a), reduction

To 0.12 g 24,33-bis-(tert-butyldimethylsilyloxy)-10-desoxy-$\Delta^{10,11}$-FK506 (title compound of Example 55) in 5 ml of tetrahydrofurane is added at −78° 0.1 ml of a 1.2N solution of diisobutylaluminium hydride in toluene and the same addition is repeated after 30 minutes. The solution is allowed to reach −10°, the excess reagent is destroyed with a few drops of water, the precipitate is filtered off and the filtrate is evaporated to dryness under reduced pressure. The residue is taken up in dichloromethane/water and the organic phase decanted. After washing with saturated sodium chloride solution and drying over magnesium sulfate the solution is evaporated to dryness. The product is purified by chromatography over silicagel using toluene/acetic acid ethyl ester 4:1 as the eluant. The title compound [9(S)-isomer] is obtained. The 9(R)-isomer is obtained as side product during chromatography:

9(S)-isomer:

$^1$H-NMR: 2.96 (ddd, $J_1$=4.5, $J_2$=8, $J_3$=11 Hz, H-32); 3.42 and 3.38 (6H and 3H, 3×OCH$_3$); 4.33 (m, H-24); 4.93 (d, J=5 Hz, H-9); 5.41 (s, H-26); 5.51 (d, J=10 Hz, H-20); 5.71 (ddt, $J_1$=10, $J_2$=17, $J_3$=6 Hz, H-37);

$^{13}$C-NMR: 67.1 (C-9); 69.5 (C-24); 105.0 (C-11); 116.4 (C-38); 122.1 (C-20); 128.8 (C-29); 132.5 (C-28); 135.7 (C-37); 138.8 (C-19); 145.0 (C-10); 169.8 (C-1); 171.6 (C-8); 210.2 (C-22);

9(R)-isomer:

$^1$H-NMR: 2.96 (ddd, $J_1$=4.5, $J_2$=8, $J_3$=11 Hz, H-32); 3.42 and 3.31 (6H and 3H, 3×OCH$_3$); 3.81 (q, J=7.5 Hz, H-21); 4.36 (m, H-24); 5.01 (d, J=5 Hz, H-9); 5.30 (s, H-26); 5.74 (ddt, $J_1$=10, $J_2$=17, $J_3$=6 Hz, H-37);

$^{13}$C-NMR: 66.3 (C-9); 70.5 (C-24); 103.7 (C-11); 116.0 (C-38); 122.8 (C-20); 129.0 (C-29); 132.4 (C-28); 136.4 (C-37); 138.6 (C-19); 144.2 (C-10); 170.0 (C-1); 171.4 (C-8); 212.3 (C-22).

dThe following further compounds of formula I are obtained in accordance with process variant a):

| Example No. | Analogously to Example No. | $R_1$ | $R_2$ | $R_3$ | $R_4$ and config. at C-9 | $R_5$ | $R_6$ | $R_7$ | n | Bonds at positions 9,10 | 10,11 | 23,24 | Physicochemical characterization data |
|---|---|---|---|---|---|---|---|---|---|---|---|---|---|
| 4[1] | 1 | OtBDMS | OtBDMS | Et | OH;(R) | OH | H | OMe | 2 | sb | sb | sb | cf; NMR* |
| 5 | 1 | OH | OtBDMS | Et | OH;(R) | OH | H | OMe | 2 | sb | sb | sb | cf; NMR* |
| 6[1] | 2 | OtBDMS | OtBDMS | Et | OH;(S) | OH | H | OMe | 2 | sb | sb | sb | cf; NMR* |
| 7[2] | 2 | OAc | OtBDMS | Et | OH;(S) | OH | H | OMe | 2 | sb | sb | sb | cf; NMR* |
| 8 | 2 | OtBDMS | absent | Et | OH;(S) | OH | H | OMe | 2 | sb | sb | db | cf; NMR* |
| 9[3] | 2 | OPiv | OtBDMS | Et | OH;(S) | OH | H | OMe | 2 | sb | sb | sb | cf; NMR* |

-continued dThe following further compounds of formula I are obtained in accordance with process variant a):

| Example No. | Analogously to Example No. | $R_1$ | $R_2$ | $R_3$ | $R_4$ and config. at C-9 | $R_5$ | $R_6$ | $R_7$ | n | Bonds at positions 9,10 | 10,11 | 23,24 | Physicochemical characterization data |
|---|---|---|---|---|---|---|---|---|---|---|---|---|---|
| 10[1] | 3 | OtBDMS | OtBDMS | Et | OH;(R) | absent | H | OMe | 2 | sb | db | sb | cf; NMR* |

*NMR:

Example 4: $^1$H-NMR: 3.42 and 3.38 and 3.35 (s + s + s, 3 × OCH$_3$); 4.28 (m, H-24); 4.38 (d, J = 11 Hz, H-9); 4.83 (m, H-2); 5.19 (s, H-26);

Example 5: $^1$H-NMR: 3.01 (ddd, J$_1$ = 4, J$_2$ = 9, J$_3$ = 12 HZ, H-32); 3.10 (d, J = 12 Hz, OH); 3.35 and 3.38 and 3.41 (s + s + s, 3 × OCH$_3$); 3.80 (dd, J$_1$ = 2, J$_2$ = 12 HZ, H-14); 3.87 (m, H-6e); 4.29 (m, H-24); 4.39 (d, J = 12 Hz, H-9); 4.83 (m H-2); 5.19 (s, H-26);

Example 6: $^1$H-NMR: 2.96 (m, C-32); 3.80 (dd, J$_1$ = 2, J$_2$ = 10 Hz, H-14); 5.35 (d, J = 2 Hz, H-26);

Example 7: $^1$H-NMR: 0.87 (s, t-butyl); 2.07 (s, OAc); 4.68 (m, H-33);

Example 8: $^1$H-NMR: 0.87 (s, t-butyl); 1.21 (s, t-butyl); 4.45 (s, H-9); 4.68 (m, H-33);

Example 9: $^1$H-NMR: 1.20 (s, t-butyl); 4.45 (s, broad, H-9); 4.68 (ddd, J$_1$ = 5, J$_2$ = 9, J$_3$ = 10 Hz, H-33);

Example 10: $^1$H-NMR: 1.80 (s, CH$_3$—C-11); 2.64 (dd, J$_1$ = 3, J$_2$ = 17 Hz, H-23); 2.90 (dd, J$_1$ = 7, J$_2$ = 17 Hz, H-23); 2.96 (ddd, J$_1$ = 4, J$_2$ = 8, J$_3$ = 11 Hz, H-32); 3.43 + 3.42 + 3.30 (s + s + s, 3 × OCH$_3$); 4.34 (quint., J = 4 Hz, H-24); 4.61 (d, J = 5 Hz, H-9 and OH) and 4.99 (d, J = 5 Hz); 5.27 (H-26).

[1]The starting material 24,33-bis-(tert-butyldimethylsilyloxy)-FR520 is obtained from FR520 in a manner analogous to 24,33-bis-(tert-butyldimethylsilyloxy)-FK506 (see Example 1);

[2]The starting material 24-tert-butyldimethylsilyloxy-33-acetyloxy-FR520 is obtained as a colourless foam in a manner analogous to Example 36, starting from 24-tert-butyldimethylsilyloxy-FR520, which is itself obtained from FR520 as follows: 0.5 g 24,33-Bis-(tert-butyldimethylsilyloxy)-FR520 [see [1] above] is dissolved at 0° under stirring in a mixture of 10 ml of acetonitrile and 0.5 ml of 40% hydrofluoric acid. After two hours at that temperature the reaction mixture is diluted with dichloromethane. After washing to neutrality with water the mixture is dried over sodium sulfate and the solvent evaporated under reduced pressure. The resultant residue is purified by column chromatography over silicagel using dichloromethane/methanol 9:1 as the eluant. 24-tert-Butyldimethylsilyloxy-FR520 is obtained as a colourless foam.

[3]The starting material 24-tert-butyldimethylsilyloxy-33-pivaloyloxy-FR520 is obtained as a colourless foam in a manner analogous to Example 36, starting from 24-tert-butyldimethylsilyloxy-FR520, [see [2] above].

The compounds of Examples 11, 14, 25, 29, 30, 32, 33, 37, 38, 39 and 64 may also be prepared in analogous manner according to process variant a).

EXAMPLE 11

9(R)-Dihydro-10-desoxy-$\Delta^{10,11}$-FK506

Formula I: $R_1,R_2$=OH; $R_3$=allyl; $R_4$=OH, (R)-configuration at C-9; $R_5$ absent; $R_6$=H; $R_7$=MeO; n=2; single bonds in positions 9,10 and 23,24; double bond in position 10,11

Process variant b), deprotection

Method 1: 0.07 g 24,33-bis-(tert-butyldimethylsilyloxy)-9(R)-dihydro-10-desoxy-$\Delta^{10,11}$-FK506 (2nd compound of Example 3) is dissolved in a mixture of 2 ml of acetonitrile and 0.04 ml of 40% aqueous hydrofluoric acid solution and the mixture is stirred at room temperature. After 18 hours the acetonitrile is evaporated under reduced pressure and the residue is extracted with dichloromethane/water. The organic phase is washed with saturated sodium chloride solution, dried over sodium sulfate and the solvent is evaporated under reduced pressure. The crude product is purified by column chromatography under pressure over silicagel using dichloromethane/methanol 95:5 as the eluant. The title compound is obtained as a colourless foam;

Method 2: 0.45 g 24,33-bis-(tert-butyldimethylsilyloxy)-9(R)-dihydro-FK506 (title compound of Example 1) is dissolved in a mixture of 8 ml of acetonitrile and 0.16 ml of 40% aqueous hydrofluoric acid solution and the mixture is stirred at room temperature. After 17 days working up is effected as under method 1 above. The title compound is obtained as a colourless foam after chromatography over silicagel using dichloromethane/methanol 95:5 as the eluant:

$^1$H-NMR: 2.83 and 2.69 (dd, J$_1$=2.5, J$_2$=18 Hz and dd, J$_1$=10, J$_2$=18 Hz, H-23); 3.01 (ddd, J$_1$=4, J$_2$=8, J$_3$=11 Hz, H-32); 3.78 (q, J=7.5, H-21); 4.14 (m, H-24); 4.52 (dd, J$_1$=3, J$_2$=6 Hz, H-2); 4.97 (d, J=6.5 Hz, H-9).

The following compounds of formula I are obtained further in accordance with process variant b) in a manner analogous to Example 11 (method 1 and method 2):

| Example No. | $R_1$ | $R_2$ | $R_3$ | $R_4$ and config. at C-9** | $R_5$ | $R_6$ | $R_7$ | n | Bonds at positions 9,10 | 10,11 | 23,24 | Physicochemical characterization data |
|---|---|---|---|---|---|---|---|---|---|---|---|---|
| 12 | OH | OH | allyl | H | OH | H | OMe | 2 | sb | sb | sb | cf; NMR* |
| 13 | OH | OH | allyl | (R) | —OC(=O)O— | H | OMe | 2 | sb | sb | sb | M.P. 132–135°; NMR* |
| 14 | OH | OtBDMS | allyl | OH (S) | OH | H | OMe | 2 | sb | sb | sb | cf; NMR* |
| 15 | OAc | OH | allyl | OAc (S) | OH | H | OMe | 2 | sb | sb | sb | cf; NMR* |
| 16 | OH | OH | allyl | OAc (S) | OH | H | OMe | 2 | sb | sb | sb | cf; NMR* |
| 17 | OH | OH | allyl | =O with $R_6$ | Cl | | OMe | 2 | sb | sb | sb | cf; NMR* |
| 18 | OH | OtBDMS | allyl | (S) | —OC(=O)O— | H | OMe | 2 | sb | sb | sb | cf; NMR* |
| 19 | OH | OH | allyl | (S) | —OC(=O)O— | H | OMe | 2 | sb | sb | sb | cf; NMR*; M.P. 198–200° |
| 20 | OAc | OH | allyl | (S) | —OC(=O)O— | H | OMe | 2 | sb | sb | sb | cf; NMR* |
| 21 | OH | OH | allyl | OAc (R) | OH | H | OMe | 2 | sb | sb | sb | cf; NMR* |
| 22 | OH | OH | allyl | =O with $R_6$ | abs. | | OMe | 2 | sb | db | sb | cf; NMR* |
| 23 | OPiv | OH | Et | (S) | —OC(=O)O— | H | OMe | 2 | sb | sb | sb | cf; NMR* |
| 24 | OH | OtBDMS | Et | (S) | —OC(=O)O— | H | OMe | 2 | sb | sb | sb | cf; NMR* |
| 25 | OPiv | OH | Et | OH (S) | OH | H | OMe | 2 | sb | sb | sb | cf; NMR* |
| 26 | OBzCl | OH | Et | (S) | —OC(=O)O— | H | OMe | 2 | sb | sb | sb | cf; NMR* |
| 27 | OAc | OH | Et | (S) | —OC(=O)O— | H | OMe | 2 | sb | sb | sb | cf; NMR* |
| 28 | OH | OH | Et | =O with $R_6$ | abs. | | OMe | 2 | sb | db | sb | cf; NMR* |
| 29 | OAc | OH | Et | OH (S) | OH | H | OMe | 2 | sb | sb | sb | cf; NMR* |
| 30 | OH | OH | Et | OH (R) | abs. | H | OMe | 2 | sb | db | sb | cf; NMR* |
| 31 | OH | absent | Et | =O with $R_6$ | abs. | | OMe | 2 | sb | db | db | cf; NMR* |
| 32 | OH | absent | Et | OH (S) | OH | H | OMe | 2 | sb | sb | db | cf; NMR* |
| 33 | OH | OH | cPropme | OH (S) | OH | H | OMe | 2 | sb | sb | sb | cf; NMR* |
| 34 | OH | OH | allyl | OAc (R) | abs. | H | OMe | 2 | sb | db | sb | cf; NMR* |

The following compounds of formula I are obtained further in accordance with process variant b) in a manner analogous to Example 11 (method 1 and method 2):

| Example No. | $R_1$ | $R_2$ | $R_3$ | $R_4$ and config. at C-9** | $R_5$ | $R_6$ | $R_7$ | n | Bonds at positions 9,10 | 10,11 | 23,24 | Physicochemical characterization data |
|---|---|---|---|---|---|---|---|---|---|---|---|---|
| 35 | OH | OH | Et | (R) | —OC(=S)O— | H | OMe | 2 | sb | sb | sb | cf; NMR* |

**Insofar as C-9 is asymmetrically substituted
*NMR:
Example 12:
$^1$H-NMR: 2.75 (d, J = 17 Hz, H-23a); 2.25 (dd, $J_1$ = 10, $J_2$ = 17 Hz, H-23b); 2.52 and 2.69 (AB-system, JAB = 15 Hz, H-9); 3.01 (ddd, $J_1$ = 5, $J_2$ = 8, $J_3$ = 11 Hz, H-32); 3.87 (dd, $J_1$ = 1, $J_2$ = 8 Hz, H-14); 4.01 (dd, $J_1$ = 3, $J_2$ = 10 Hz, H-24); 4.97 (m, H-2); 5.21 (s, broad, H-26);
$^{13}$C-NMR: 98.4 (C-10); 116.5 (C-38); 121.4 (C-20); 128.9 (C-29); 132.4 (C-28); 35.4 (C-37); 141.1 (C-19) 169.3 (C-1); 173.9 (C-8); 213.99 (C-22);
Example 13:
$^1$H-NMR: 2.76 and 2.60 (dd, $J_1$ = 1.5, $J_2$ = 18 Hz and dd, $J_1$ = 10, $J_2$ = 18 Hz, H-23); 3.01 (ddd, $J_1$ = 5, $J_2$ = 8, $J_3$ = 11 Hz, H-32); 3.42 and 3.39 and 3.29 (s + s + s, 3 × OCH$_3$); 3.60 (dd, $J_1$ = 1, $J_2$ = 8 Hz, H-14); 3.83 (dt, $J_1$ = 5, $J_2$ = 8 Hz, H-21); 4.17 (m, H-24); 4.66 (dd, $J_1$ = 2.5, $J_2$ = 6 Hz, H-2); 5.16 (s, broad, H-26) 5.33 (s, H-9);
$^{13}$C-NMR: 105.5 (C-10); 116.3 (C-38); 122.2 (C-20); 128.5 (C-29); 131.9 (C-28); 136.0 (C-37); 138.6 (C-19); 152.2 (O—CO—O); 163.6 (C-8); 169.7 (C-1); 2.14.7 (C-22);
Example 14:
$^1$H-NMR: 3.81 (dd, $J_1$ = 1, $J_2$ = 11 Hz, H-14); 4.22 (m, H-24); 4.43 (s, broad, H-9); 5.15 (d, J = 3 Hz, H-26);
$^{13}$C-NMR: 99.6 (C-10); 115.8 (C-38); 122.1 (C-20); 130.2 (C-29); 133.2 (C-28); 136.1 (C-37); 140.3 (C-19); 169.4 (C-1), 173.6 (C-8); 209.5 (C-22);
Example 15: $^1$H-NMR: 2.18 and 2.08 (s + s, 2 × OAc); 4.68 (ddd, $J_1$ = 5, $J_2$ = 9, $J_3$ = 10 Hz, H-33); 5.60 (s, H-9);
Example 16: $^1$H-NMR: 2.18 (s, OAc); 3.02 (ddd, $J_1$ = 4, $J_2$ = 9, $J_3$ = 11 Hz, H-32); 3.42 and 3.40 and 3.38 (s + s + s, 3 × OCH$_3$); 5.60 (s, H-9);
Example 17:
$^1$H-NMR: 3.02 (ddd, $J_1$ = 4, $J_2$ = 9, $J_3$ = 12 Hz, H-32); 3.42 and 3.35 (s + s, 6 H and 3 H, 3 × OCH$_3$; 3.93 (dd, $J_1$ = 2.5, $J_2$ = 10 Hz, H-14); 4.80 (d, J = 10 Hz, H-20); 5.03 and 4.98 (H-38); 5.11 (d, J = 10 Hz, H-29); 5.16 (H-26); 5.26 (H-2); 5.70 (ddt, $J_1$ = 10, $J_2$ = 17, $J_3$ = 6 Hz, H-37);
$^{13}$C-NMR: 108.7 (C-10); 116.4 (C-38); 122.5 (C-20); 129.3 (C-29); 132.1 (C-28); 135.6 (C-37); 140.2 (C-19); 164.0 (C-8), 169.1 (C-1); 189.2 (C-9); 211.8 (C-22);
Example 18: $^1$H-NMR: 0.055 (6 H, Si—CH$_3$); 0.87 (s, t-Bu); 3.02 (ddd., $J_1$ = 4, $J_2$ = 9, $J_3$ = 12 Hz, H-32); 3.40 and 3.32 (s + s, 6 H and 3H, 3 × OCH$_3$); 3.62 (dd, $J_1$ = 5, $J_2$ = 11 Hz, H-15); 3.70 (d, J = 9 Hz, H-14); 4.12 (m, H-24); 4.57 (d, J = 13 Hz, H-6e); 4.97 (s H-9); 5.34 (d, J = 9 Hz, H-29); 5.47 (d, J = 4 Hz, H-26); 5.67 (ddt, $J_1$ = 10, $J_2$ = 17, $J_3$ = 6 Hz, H-37);
Example 19:
$^1$H-NMR: 3.03 (ddd, $J_1$ = 4, $J_2$ = 9, $J_3$ = 12 Hz, H-32); 3.44 and 3.41 and 3.35 (s + s + s, 3 × OCH$_3$); 4.12 (m, H-24); 4.55 (d, broad, J = 13 Hz, H-6e); 4.80 (d, broad, J = 3 Hz, H-2); 5.09 (s, H-9); 5.53 (s, broad, H-26); 5.70 (ddt, $J_1$ = 10, $J_2$ = 17, $J_3$ = 6 Hz, H-37);
$^{13}$C-NMR: 81.9 (C-9); 106.5 (C-10); 116.8 (C-38); 123.4 (C-20); 129.2 (C-29); 132.3 (C-28); 135.2 (C-37); 140.1 (C-19); 151.5 (O—CO—O); 163.0 (C-8), 168.9 (C-1); 210.0 (C-22);
Example 20: $^1$H-NMR: 2.09 (s, OAc); 3.24 (ddd, $J_1$ = 4, $J_2$ = 9, $J_3$ = 12 Hz, H-32); 3.41 and 3.35 (6 H and 3H, 3 × OCH$_3$); 4.12 (m, H-24); 4.56 (d, broad, J = 13 Hz, H-6e); 4.69 (ddd, $J_1$ = 5, $J_2$ = 9, $J_3$ = 10 Hz, H-33); 4.80 (d, broad, J = 3 Hz, H-2); 5.08 (s, H-9); 5.51 (s, broad, H-26); 5.70 (ddt, $J_1$ = 10, $J_2$ = 17, $J_3$ = 6 Hz, H-37);
Example 21: $^1$H-NMR: 2.13 (s, OAc); 3.44 and 3.41 and 3.34 (s + s + s, 3 × OCH$_3$); 3.01 (ddd, $J_1$ = 5, $J_2$ = 8, $J_3$ = 11 Hz, H-32, 4.07 (m, H-24); 5.75 (ddt, $J_1$ = 10, $J_2$ = 17, $J_3$ = 6 Hz, H-37); 6.14 (s, H-9);
Example 22:
$^1$H-NMR: 2.00 (s, broad, CH$_3$ on C-11); 2.70 (dd, $J_1$ = 6.5, $J_2$ = 18 Hz, H-12); 3.00 (ddd, $J_1$ = 4.5, $J_2$ = 8, $J_3$ = 11 Hz, H-32); 3.24 (dt, $J_1$ = 6, $J_2$ = 9 Hz, H-21); 3.78 (dt, $J_1$ = 7, $J_2$ = 9 Hz, H-13); 3.95 (dd, $J_1$ = 4.5, $J_2$ = 10 Hz, H-24); 5.33 (s, H-26); 5.46 (d, J = 10 Hz, H-20); 5.68 (ddt, $J_1$ = 10, $J_2$ =17, $J_3$ = 6 Hz, H-37);
$^{13}$C-NMR: 116.2 (C-38); 122.2 (C-20); 125.7 (C-11); 128.0 (C-28); 136.2 (C-37); 137.9 (C-19); 143.4 (C-10); 167.1 (C-8); 168.5 (C-1); 186.9 (C-9); 213.9 (C-22);
Example 23: $^1$H-NMR: 1.21 (s, t-butyl); 3.11 (q, J = 8 Hz, H-21); 3.24 (ddd, $J_1$ = 4, $J_2$ = 8, $J_3$ = 10 Hz, H-32); 3.40 + 3.40 + 3.34 (s + s + s, 3 × CH$_3$O); 4.15 (m, H-24); 4.56 (d, br, J = 13 Hz, H-6e); 4.68 (ddd, $J_1$ = 4, $J_2$ = 8, $J_3$ = 10 Hz, H-33); 4.80 (d, br, J = 4 Hz, H-2); 4.98 (d, J = 10 Hz, H-20); 5.52 (s, H-26); 5.11 (d, J = 9 Hz, H-29); 5.09 (s, H-9);
Example 24: $^1$H-NMR: 0.05 (Me$_3$ Si): 0.86 (s, t-butyl); 3.01 (ddd, $J_1$ = 4, $J_2$ = 8, $J_3$ = 1 Hz, H-32); 3.61 (dd, $J_1$ = 4, $J_2$ = 11 Hz, H-15); 3.69 (d, J = 10 Hz, H-14); 4.12 (m, H-24); 4.56 (d, br, J = 13 Hz, H-6e); 4.98 (s, H-9); 5.33 (d, J = 9 Hz, H-29); 5.44 (d, J = 4 Hz, H-26);
Example 25: $^1$H-NMR: 1.21 (s, t-butyl); 4.04 (d, J = 7 Hz, 9-OH); 4.18 (d, J = 7 Hz, H-9); 4.68 (m, H-32);
Example 26: $^1$H-NMR: 3.11 (q, J = 8 Hz, H-21); 3.42 + 3.42 + 3.36 (s + s + s, 3 × OCH$_3$); 4.16 (m, H-24); 4.57 (d, br, J = 13 Hz, H-6e); 4.81 (H-2); 5.11 (s, H-9); 5.14 (d, J = 9 Hz, H-29); 5.54 (s, H-26); 8.0 and 7.44 (AA'BB'-system, ClC$_6$H$_4$CO). At 333° K. are also detectable: 4.95 (ddd, $J_1$ = 4, $J_2$ = 8, $J_3$ = 10 Hz, H-33); 5.00 (d, J = 10 Hz, H-20);
Example 27: $^1$H-NMR: 2.08 (s, OAc); 4.54 (d, J = 13 Hz, H-6e); 4.69 (m, H-33); 5.12 (s, H-9); 5.54 (H-26);
Example 28: $^1$H-NMR: 3.02 (ddd, $J_1$ = 4, $J_2$ = 8, $J_3$ = 10 Hz, H-32);
Example 29: $^1$H-NMR: 4.69 (m, H-33); 2.08 (s, OAc);
Example 30: $^1$H-NMR: 1.79 (s, CH$_3$—C—11); 2.41 (dd, $J_1$ = 5, $J_2$ = 16 Hz, H-12); 2.70 (dd, $J_1$ = 9, $J_2$ = 17 Hz, H-23a); 2.84 (dd, $J_1$ = 2, $J_2$ = 17 Hz, H-23b); 3.01 (ddd, $J_1$ = 4, $J_2$ = 8, $J_3$ = 11 Hz, H-32); 4.13 (t, J = 8 Hz, H-24); 4.33 (d, J = 5 Hz, —OH); 4.53 (dd, $J_1$ = 3, $J_2$ = 6 Hz, H-2); 4.96 (d, J = 5 Hz, H-9); 5.02 (d, J = 2.5 Hz, H-26); 5.33 (d, J = 8 Hz, H-29);
Example 31: $^1$H-NMR: 1.66 + 1.77 (s + s, CH$_3$—C-19, CH$_3$—C-28); 2.05 (s, CH$_3$—C-11); 6.23 (dd, $J_1$ = 1, n = 15 Hz, H-23); 6.68 (dd, $J_1$ = 8, $J_2$ = 15 Hz, H-24);
Example 32: $^1$H-NMR: (1/1 mixture) 3.70 (d, J = 9 Hz) and 3.83 (dd, $J_1$ = 1.5, $J_2$ = 9 Hz, H-14); 6.15 (dd, $J_1$ = 1, $J_2$ = 15 Hz) and 6.23 (dd, $J_1$ = 1.5, $J_2$ = 15 Hz, H-23); 6.72 (dd, $J_1$ = 7, $J_2$ = 15 Hz) and 6.85 (dd, $J_1$ = 6, $J_2$ = 15 Hz, H-24);
Example 33: $^1$H-NMR: 0.05–0.15 (m, 2 H, cyclopropyl); 0.4–0.5 (m, 2 H, cyclopropyl); 0.60–0.75 (m, 1 H, cyclopropyl);
Example 34: $^1$H-NMR: 1.13 (d, J = 7 Hz, CH$_3$—C-11); 3.29, 3.39 and 3.42 (s + s + s, 3 × OCH$_3$); 4.15 (m, br, H-24); 4.65 (dd, $J_1$ = 1, $J_2$ = 5 Hz, H-2); 4.96 (d, J = 9 Hz, H-20); 5.11 (d, J = 10 Hz, H-29); 5.13 (s, H-26); 5.47 (s, H-9);
Example 35: $^1$H-NMR: 2.73 (d, J = 2 Hz, H-23); 2.96 (ddd, $J_1$ = 5, $J_2$ = 9, $J_3$ = 11 Hz, H-32); 3.29 and 3.39 and 3.42 (s + s + s, 3 × OCH$_3$); 3.67 (d, J = 10 Hz, H-14); 4.17 (m, H-24); 4.65 (m, H-2); 5.13 (s, broad, H-26); 5.47 (s, H-9).
The compounds of Examples 5, 7, 9, 36 to 39, 52, 59, 61, 62, 64 and 65 may be prepared in analogous manner according to process variant b).

EXAMPLE 36

24-tert-Butyldimethylsilyoxy-9(S)-dihydro-FK506-9,33-diacetate

Formula I: $R_1, R_4$=OAc, (S)-configuration at C-9; $R_2$=OtBDMS; $R_3$=allyl; $R_5$=OH; $R_6$=H; $R_7$=MeO; n=2; single bonds in positions 9,10; 10,11 and 23,24

Process variant c), acylation 0.1 g 24-tert-butyldimethylsilyloxy-9(S)-dihydro-FK506 (compound of Example 14) is stirred for 30 minutes at room temperature with a mixture of 0.3 ml of acetanhydride and 10 mg 4-dimethylaminopyridine in 3 ml of pyridine. The reaction mixture is evaporated to dryness under reduced pressure, the residue taken up in acetic acid ethyl ester/water and the organic phase decanted. After washing with dilute hydrochloric acid and water the organic phase is dried over magnesium sulfate and evaporated to dryness under reduced pressure. The resultant product can be purified by chromatography over silicagel using dichloromethane/ethanol 95:5 as the eluant. The title compound is obtained:

$^1$H-NMR: 0.03 and −0.03 (s+s, 2×SiCH$_3$); 0.87 (s, t-Bu); 2.19 and 2.08 (s+s, 2×OAc); 3.40 and 3.39 and 3.38 (s+s+s, 3×OCH$_3$); 4.19 (m, H-24); 4.69 (m, H-33); 5.62 (s, H-9).

The following compounds of formula I are obtained further in accordance with process variant c) in a manner analogous to Example 36:

| Example No. | R$_1$ | R$_2$ | R$_3$ | R$_4$ and config. at C-9 | R$_5$ | R$_6$ | R$_7$ | n | Bonds at positions 9,10 | 10,11 | 23,24 | Physicochemical characterization data |
|---|---|---|---|---|---|---|---|---|---|---|---|---|
| 37 | OPiv | absent | Et | OH (S) | OH | H | OMe | 2 | sb | sb | db | cf |
| 38 | OiBu | absent | Et | OH (S) | OH | H | OMe | 2 | sb | sb | db | cf |
| 39 | OAc | absent | Et | OH (S) | OH | H | OMe | 2 | sb | sb | db | cf |
| 40 | OtBDMS | OtBDMS | allyl | OAc (S) | OH | H | OMe | 2 | sb | sb | sb | cf; NMR* |
| 41 | OtBDMS | OtBDMS | allyl | OAc (R) | OH | H | OMe | 2 | sb | sb | sb | cf; NMR* |
| 42 | OAc | OtBDMS | allyl | (S) | —OC(=O)O— | H | OMe | 2 | sb | sb | sb | cf; NMR* |
| 43 | OtBDMS | OtBDMS | allyl | OAc (R) | abs. | H | OMe | 2 | sb | db | sb | cf; NMR* |
| 44 | OPiv | OtBDMS | Et | (S) | —OC(=O)O— | H | OMe | 2 | sb | sb | sb | cf; NMR* |
| 45 | OBzCl | OtBDMS | Et | (S) | —OC(=O)O— | H | OMe | 2 | sb | sb | sb | cf; NMR* |
| 46 | OAc | OtBDMS | Et | (S) | —OC(=O)O— | H | OMe | 2 | sb | sb | sb | cf; NMR* |

*NMR:

Example 40: $^1$H-NMR: 0.06 and 0.05 and 0.00 and −0.04 (4 × SiCH$_3$); 0.87 and 0.85 (s + s, 2xt-Bu); 2.17 (s, OAc), 3.39 and 3.38 and 3.36 (s + s + s, 3 × OCH$_3$); 4.18 (m, H-24); 5.60 (s, H-9);

Example 41:
$^1$H-NMR: 2.15 (s, OAc); 3.84 (dd, J$_1$ = 2, J$_2$ = 9 Hz, H-14); 4.05 (d, br, J = 13 Hz, H-6e); 4.32 (quintet, J = 3 Hz, H-24); 5.17 (s, (H-26); 5.33 (d, J = 10 Hz, H-29); 5.71 (s, H-9); 5.79 (ddt, J$_1$ = 7, J$_2$ = 10, J$_3$ = 17 Hz, H-37);
$^{13}$C-NMR: 98.1 (C-10); 116.0 (C-38); 121.7 (C-20); 128.3 (C-29); 132.5 (C-28); 136.4 (C-37); 139.2 (C-19); 167.8 (OAc); 169.8 (C-1), 170.6 (C-8); 210.4 (C-22);

Example 42: $^1$H-NMR: 0.05 (s, SiCH$_3$); 0.85 (s, t-Bu); 2.08 (s, OAc); 3.23 (ddd, J$_1$ = 4, J$_2$ = 9, J$_3$ = 12 Hz, H-32); 3.40 and 3.38 and 3.31 (s + s + s, 3 × OCH$_3$); 4.12 (m, H-24); 4.55 (d, broad, J = 13 Hz, H-6e); 4.69 (ddd, J$_1$ = 5, J$_2$ = 9, J$_3$ = 10 Hz, H-33); 4.98 (s, H-9); 5.30 (d, J = 9 Hz, H-29); 5.44 (d, J = 4 Hz, H-26); 5.67 (ddt, J$_1$ = 10, J$_2$ = 17, J$_3$ = 6 Hz, H-37);

Example 43: $^1$H-NMR: 2.11 (s, OAc); 3.44 and 3.41 and 3.32 (s + s + s, 3 × OCH$_3$); 2.96 (ddd, J$_1$ = 4.5, J$_2$ = 8, J$_3$ = 11 Hz, H-32); 3.80 (q, J = 7 Hz, H-21); 4.33 (m, H-24); 4.62 (m, H-2); 5.26 (s, H-26); 5.73 (ddt, J$_1$ = 10, J$_2$ = 17, J$_3$ = 6 Hz, H-37); 6.11 (s, H-9);

Example 44: $^1$H-NMR: 0.05 (s, SiCH$_3$); 0.87 (s, t-butyl); 1.21 (s, t-butyl; 3.40 + 3.38 + 3.30 (s + s + s, 3 × OCH$_3$); 4.12 (m, H-24); 4.57 (d, br, J = 13 Hz, H-6e); 4.68 (ddd, J$_1$ = 4, J$_2$ = 8; J$_3$ = 10 Hz, H-33); 5.00 (s, H-9); 5.32 (d, J = 9 Hz, H-29); 5.42 (d, J = 5 Hz, H-26);

Example 45: $^1$H-NMR: 3.40 + 3.38 + 3.30 (s + s + s, 3 × OCH$_3$); 4.12 (m, H-24); 4.57 (d, br, J = 13 Hz, H-6e); 5.00 (s, H-9); 5.34 (d, J = 9 Hz, H-29); 5.42 (d, J = 5 Hz, H-26); 7.99 and 7.43 (AA'BB'-system, ClC$_6$H$_4$CO);

Example 46: $^1$H-NMR: 2.08 (s, OAc); 4.57 (d, J = 13 Hz, H-6e); 4.70 (m, H-33); 5.00 (s, H-9); 5.30 (d, J = 9 Hz); 5.41 (d, J = 4 Hz, H-26).

The compounds of Examples 7, 9, 15, 16, 20, 21, 23, 25 to 27, 34, 62 and 63 may be prepared in analogous manner according to process variant c).

EXAMPLE 47

24,33-Bis-(tert-butyldimethylsilyloxy)-9(R)-dihydro-FK506-9,10-carbonate

Formula I: R$_1$, R$_2$=OtBDMS; R$_3$=allyl; R$_4$+R$_5$=—OC(=O)O—, (R)-configuration at C-9; R$_6$=H; R$_7$=MeO; n=2; single bonds in positions 9,10; 10,11 and 23,24

Process variant d), reaction with N,N'-carbonyl- or N,N'-thiocarbonyldiimidazole 1 g 24,33-bis-(tert-butyldimethylsilyloxy)-9(R)-dihydro-FK506 (title compound of Example 1) is dissolved in 15 ml of 1,2-dichloroethane and 0.188 g N,N'-carbonyldiimidazole is added in portions to the mixture while stirring. After 18 hours stirring at room temperature the solvent is evaporated under reduced pressure and the resultant residue is purified by chromatography under pressure over silicagel using hexane/acetic acid ethyl ester 3:1 as the eluant. The title compound is obtained as a colourless foam:

$^1$H-NMR: 2.65 (d, J=5 Hz, H-23); 2.96 (ddd, J$_1$=5, J$_2$=8, J$_3$=11 Hz, H-32); 3.43 and 3.40 and 3.30 (s+s+s, 3×OCH$_3$); 3.62 (dd, J$_1$=1, J$_2$=8 Hz, H-14); 3.86 (dt, J$_1$=5, J$_2$=7.5 Hz, H-21); 4.37 (q, J=5 Hz, H-24); 4.81 (dd, J$_1$=ca. 2.5, J$_2$=5 Hz, H-2); 5.29 (s, broad, H-26); 5.33 (s, H-9);

$^{13}$C-NMR: 105.6 (C-10); 116.1 (C-38); 122.8 (C-20); 128.1 (C-29); 132.5 (C-28); 136.4 (C-37); 138.9 (C-19); 152.2 (O-CO-O); 163.2 (C-8); 169.5 (C-1); 212.2 (C-22).

The following compounds of formula I are obtained further in accordance with process variant d) in a manner analogous to Example 47:

| Example No. | R$_1$ | R$_2$ | R$_3$ | R$_4$ and config. at C-9 | R$_5$ | R$_6$ | R$_7$ | n | Bonds at positions 9,10 | 10,11 | 23,24 | Physicochemical characterization data |
|---|---|---|---|---|---|---|---|---|---|---|---|---|
| 48 | OtBDMS | OtBDMS | allyl | (R) | —OC(=S)O— | H | OMe | 2 | sb | sb | sb | cf; NMR* |
| 49 | OtBDMS | OtBDMS | allyl | (S) | —OC(=S)O— | H | OMe | 2 | sb | sb | sb | cf; NMR* |
| 50 | OtBDMS | OtBDMS | allyl | (S) | —OC(=O)O— | H | OMe | 2 | sb | sb | sb | cf; NMR* |
| 51 | OtBDMS | OtBDMS | Et | (S) | —OC(=O)O— | H | OMe | 2 | sb | sb | sb | cf; NMR* |

| | | | | R₄ and | | | | | Bonds at positions | | | |
|---------|----|--------|----|-----------|----|----|----|---|------|-------|-------|----------------|
| Example | | | | config. | | | | | | | | Physicochemical |
| No. | R₁ | R₂ | R₃ | at C-9 | R₅ | R₆ | R₇ | n | 9,10 | 10,11 | 23,24 | characterization data |
| 52 | OH | OtBDMS | Et | (R) | —OC(=S)O— | H | OMe | 2 | sb | sb | sb | cf; NMR* |

*NMR:
Example 48:
¹H-NMR: 2.66 (d, J = 5 Hz, 2H, H-23); 2.96 (ddd, J₁ = 5, J₂ = 8, J₃ = 11 Hz, H-32); 3.42 and 3.40 and 3.30 (s + s + s, 3 × OCH₃); 3.68 (dd, J₁ = 1, J₂ = 8 Hz, H-14); 3.86 (dt, J₁ = 5, J₂ = 7.5 Hz, H-21); 4.36 (q, J = 4 Hz, H-24); 4.80 (m, H-2); 5.28 (s, broad, H-26); 5.48 (s, H-9);
¹³C-NMR: 79.7 (C-9); 111.2 (C-10); 115.9 (C-38); 122.5 (C-20); 132.2 (C-28); 128.0 (C-29); 136.3 (C-37); 139.0 (C-19); 162.2 (C-8); 169.2 (C-1); 189.3 (O—CS—O); 211.7 (C-22);

Example 49:
¹H-NMR: 2.95 (ddd, J₁ = 4, J₂ = 9, J₃ = 12 Hz, H-32); 3.40 + 3.30 (s + s, 6H and 3H, 3 × OCH₃); 3.62 (dd, J₁ = 5, J₂ = 11 Hz, H-15); 3.75 (d, J = 9 Hz, H-14); 4.12 (m, H-24); 4.54 (d, J = 13 Hz, H-6e); 4.88 (H-2); 4.91 (d, J = 10 Hz, H-20); 5.02 and 4.96 (H-38); 5.11 (s H-9); 5.30 (d, J = 9 Hz, H-29); 5.46 (d, J = 4 Hz, H-26); 5.67 (ddt, J₁ = 10, J₂ = 17, J₃ = 6 Hz, H-37);
¹³C-NMR: 85.3 (C-9); 111.8 (C-10); 116.7 (C-38); 124.2 (C-20); 132.3 (C-28); 134.8 (C-29); 135.3 (C-37); 137.7 (C-19); 161.4 (C-8); 169.0 (C-1); 188.5 (O—CS—O); 209.5 (C-22);

Example 50:
¹H-NMR: 2.95 (ddd, J₁ = 4, J₂ = 9, J₃ = 12 Hz, H-32); 3.40 and 3.30 (s + s, 6H and 3H, 3 × OCH₃); 3.61 (dd, J₁ = 5, J₂ = 11 Hz, H-15); 3.69 (d, J = 9 Hz, H-14); 4.13 (m, H-24); 4.55 (d, J = 13 Hz, H-6e); 4.96 (H-9); 5.31 (d, J = 9 Hz, H-29); 5.45 (d, J = 4 Hz, H-26); 5.67 (ddt, J₁ = 10, J₂ = 17, J₃ = 6 Hz, H-37);
¹³C-NMR: 82.1 (C-9); 106.6 (C-10); 116.8 (C-38); 124.3 (C-20); 132.4 (C-28); 135.0 (C-29); 135.3 (C-37); 137.6 (C-19); 151.4 (O—CO—O); 162.3 (C-8); 169.2 (C-1); 209.6 (C-22);

Example 51: ¹H-NMR: 3.61 (dd, J₁ = 4, J₂ = 11 Hz, H-15); 3.69 (d, J = 10 Hz, H-14); 4.11 (m, H-24); 4.56 (d, br, J = 13 Hz, H-6e); 4.93 (d, br, J = 6 Hz); 4.98 (s, H-9); 5.31 (d, J = 9 Hz, H-29); 5.44 (d, J = 4 Hz, H-26);

Example 52: ¹H-NMR: 1.13 (d, J = 7 Hz, CH₃—C-11); 4.37 (m, H-24); 5.27 (s, H-26); 5.47 (s, H-9).

The compounds of Examples 13, 18 to 20, 23, 24, 27, 35, 42 and 44 to 46 may be prepared in analogous manner according to process variant d).

EXAMPLE 53

24,33-Bis-(tert-butyldimethylsilyloxy)-10-chloro-10-desoxy-FK506

Formula I: R₁, R₂=OtBDMS; R₃=allyl; R₄+R₆=oxo; R₅=Cl; R₇=MeO; n=2; single bonds in positions 9,10; 10,11 and 23,24

Process variant e), halogenation

To 0.1 g 24,33-bis-(tert-butyldimethylsilyloxy)-FK506 (see under Example 1) in 4 ml of diethylether is added about 20 mg pyridine and 25 mg thionyl chloride and the mixture is stirred at room temperature for 1 hour. The reaction mixture is evaporated to dryness, the residue taken up in acetic acid ethyl ester, the solution filtered and washed with saturated sodium chloride solution. After drying over magnesium sulfate the solvent is evaporated. The title compound is obtained:

¹H-NMR: 2.94 (ddd, J₁=4, J₂=9, J₃=12 Hz, H-32); 3.42 and 3.40and 3.37 (s+s+s, 3×OCH₃); 3.96 (dd, J₁=2.5, J₂=10 Hz, H-14); 4.07 (dt, J₁=2.5 Hz, J₂=10 Hz, H-24); 4.66 (d, J=10 Hz, H-20); 4.93 (dd, J₁=2, J₂=10 Hz, H-38c); 4.98 (dd, J₁=2, J₂=17 Hz, H-38tr); 5.17 (d, J=10 Hz, H-29); 5.19 (H-2); 5.51 (d, J=1 Hz, H-26); 5.66 (ddt, J₁=10, J₂=17, J₃=6 Hz, H-37);

¹³C-NMR: 108.7 (C-10); 115.8 (C-38); 121.9 (C-20); 132.4 (C-29); 133.3 (C-28); 136.2 (C-37); 140.7 (C-19); 163.7 (C-8); 168.9 (C-1); 188.8 (C-9); 210.0 (C-22).

EXAMPLE 55

24,33-Bis-(tert-butyldimethylsilyloxy)-10-desoxy-Δ¹⁰,¹¹-FK506

Formula I: R₁, R₂=OtBDMS; R₃=allyl; R₄+R₆=oxo; R₅ absent; R₇=MeO; n=2; single bonds in positions 9,10 and 23,24; double bond in position 10,11

Process variant f), splitting off hydrogen halide

A mixture of 0.2 g 24,33-bis-(tert-butyldimethylsilyloxy)-10-chloro-10-desoxy-FK506 (title compound of Example 53) and 0.1 ml of 1,8-diazabicyclo[5.4.0]undec-7-ene is stirred for 48 hours at room temperature in 10 ml of tetrahydrofurane. The resultant mixture is evaporated to dryness under reduced pressure and the residue taken up in acetic acid ethyl ester/water. The organic phase is separated, washed with saturated sodium chloride solution and dried over magnesium sulfate. The solvent is distilled off under reduced pressure and the resultant product purified by chromatography over silicagel using toluene/acetic acid ethyl ester 4:1 as the eluant. The title compound is obtained:

¹H-NMR: 2.06 (s, broad, CH₃-C-11); 2.73 (dd, J₁=6.5, J₂=18 Hz, H-12); 2.96 (ddd, J₁=4.5, J₂=8, J₃=11 Hz, H-32); 3.18 (dt, J₁=6, J₂=9 Hz, H-21); 3.80 (dt, J₁=7, J₂=9 Hz, H-13); 4.31 (m, H-24); 5.16 (d, J=5 Hz, H-2); 5.34 (s, H-26) 5.68 (ddt, J₁=10, J₂=17, J₃=6 Hz, H-37); 5.84 (d, J=10 Hz, H-20);

¹³C-NMR: 116.3 (C-38); 124.0 (C-20); 125.7 (C-11); 128.4 (C-29); 132.8 (C-28); 135.7 (C-37); 137.9 (C-19); 143.7 (C-10); 166.7 (C-8); 168.3 (C-1); 187.2 (C-9); 210.6 (C-22).

| | | | | | | | | | Bonds at positions | | | |
|---------|--------|--------|----|----|----|----|-----|---|------|-------|-------|----------------|
| Example | | | | | | | | | | | | Physicochemical |
| No. | R₁ | R₂ | R₃ | R₄ | R₅ | R₆ | R₇ | n | 9,10 | 10,11 | 23,24 | characterization data |
| 54 | OtBDMS | OtBDMS | Et | =O with R₆ | | Cl | MeO | 2 | sb | sb | sb | cf; NMR* |

*NMR: ¹H-NMR: 0.888 and 0.86 (t-butyl); 2.94 (ddd, J₁ = 4, J₂ = 8, J₃ = 11 Hz, H-32); 3.96 (dd, J₁ = 9, J₂ = 2.5 Hz, H-14); 4.06 (dt, J₁ = 10, J₂ = 2.5 Hz, H-24); 4.62 (d, J = 10 Hz, H-20); 5.51 (H-26).

The compound of Example 17 may also be prepared in analogous manner according to process variant e).

The following compound of formula I are obtained further in accordance with process variant f) in a manner analogous to Example 55:

| Example No. | R$_1$ | R$_2$ | R$_3$ | R$_4$ | R$_5$ | R$_6$ | R$_7$ | n | Bonds at positions 9,10 | 10,11 | 23,24 | Physicochemical characterization data |
|---|---|---|---|---|---|---|---|---|---|---|---|---|
| 56 | OtBDMS | OtBDMS | Et | =O with R$_6$ | abs. | | MeO | 2 | sb | db | sb | cf; NMR* |

*NMR: $^1$H-NMR: 2.06 (s, CH$_3$—C-11); 2.96 (ddd, J$_1$ = 4, J$_2$ = 8, J$_3$ = 10 Hz, H-32); 3.07 (dt, J$_1$ = 6, J$_2$ = 10 Hz, H-21); 4.27 (m, H-24); 5.02 (d, J = 9 Hz, H-20); 5.07 (d, br, J = 5 Hz, H-2); 5.20 (s, H-26); 5.32 (d, J = 10 Hz, H-29).
The compounds of Examples 10, 11, 22, 28, 30, 31, 34 and 43 may also be prepared in analogous manner according to process variant f).

EXAMPLE 57

24,33-Bis-(tert-butyldimethylsilyloxy)-9-dihydro-9-O-methyl-FK506-9,10-carbonate Formula I: R$_1$, R$_2$=OtBDMS; R$_3$=allyl; R$_4$+R$_5$=—OC(=O)O—; R$_6$, R$_7$=MeO; n=2; single bonds in positions 9,10; 10,11 and 23,24

Process variant g), reaction with a hydrogen carbonate 0.1 g 24,33-bis-(tert-butyldimethylsilyloxy)-10-chloro-10-desoxy-FK506 (title compound of Example 53) is reacted with about 0.04 g sodium hydrogen carbonate in 4 ml of methanol for 6 hours at 60° and the mixture is stirred thereafter at room temperature for 48 hours. The reaction mixture is filtered, the solvent evaporated under reduced pressure and the crude product purified by chromatography over silicagel using toluene/acetic acid ethyl ester 4:1 as the eluant. The title compound is obtained:

$^1$H-NMR: 2.62 (dd, J$_1$=3, J$_2$=17 Hz, H-23a); 2.82 (dd, J$_1$=7.5, J$_2$=17 Hz, H-23b); 2.96 (ddd, J$_1$=4, J$_2$=9, J$_3$=11 Hz, H-32); 3.64, 3.42, 3.38 and 3.30 (s+s+s+s, 4×OCH$_3$); 4.34 (m, H-24); 4.71 (m, H-2); 5.24 (s, H-26); 5.74 (ddt, J$_1$=10, J$_2$=17, J$_3$=6 Hz, H-37);

$^{13}$C-NMR: 107.2 and 109.3 (C-9 and C-10); 116.1 (C-38); 122.5 (C-20); 127.9 (C-29); 132.3 (C-28); 136.3 (C-37); 138.6 (C-19); 150.2 (O—CO—O); 162.3 (C-8); 169.9 (C-1); 212.2 (C-22).

EXAMPLE 58

10-desoxy-Δ$^{9,10}$-24,33-bis-(tert-butyldimethylsilyloxy)-FK506

Formula I: R$_1$, R$_2$=OtBDMS; R$_3$=allyl; R$_4$, R$_5$ absent; R$_6$=H; R$_7$=MeO; n=2; single bonds in 10,11 and 23,24 positions; double bond in 9,10 position Process variant h), radical deoxygenation 1.08 g 24,33-bis-(tert-butyldimethylsilyloxy)-9(R)-dihydro-FK506-9,10-thiocarbonate (compound of Example 48) is dissolved in 50 ml of toluene and the mixture is reacted with 0.53 ml of tributyl tin hydride and 1 mg azoisobutyronitrile and the resulant mixture is heated under refluxing for 15 minutes. The solution is cooled to room temperature and the solvent evaporated under reduced pressure. The resultant residue is purified by column chromatography over silicagel using hexane/diethylether 1:1 as the eluant. The title compound is obtained as a colourless foam:

$^1$H-NMR: 5.37 (s, H-9);

$^{13}$C-NMR: two isomers 102.5 and 96.1 (C-9); 116.4 and 115.6 (C-38); 123.6 and 120.9 (C-20); 133.3 and 128.8 (C-29); 133.0 and 131.5 (C-18); 136.6 and 135.6 (C-37); 139.9 and 138.8 (C-19); 166.7 and 163.5 (C-8); 169.3 and 167.8 (C-1); 172.1 and 170.1 (C-10); 210.8 and 208.3 (C-22).

The following compound of formula I are obtained further in accordance with process variant h) in a manner analogous to Example 58:

| Example No. | R$_1$ | R$_2$ | R$_3$ | R$_4$ | R$_5$ | R$_6$ | R$_7$ | n | Bonds at positions 9,10 | 10,11 | 23,24 | Physicochemical characterization data |
|---|---|---|---|---|---|---|---|---|---|---|---|---|
| 59 | OH | OtBDMS | Et | absent | abs. | H | MeO | 2 | db | sb | sb | cf; NMR* |

*NMR: $^1$H-NMR: 1.36 (d, J = 7 Hz, CH$_3$—C-11); 3.89 (dd, J$_1$ = 1, J$_2$ = 9 Hz, H-14); 4.04 (m, H-24); 4.51 (d, br, J = 13 Hz, H-6e); 4.65 (d, br, J = 4 Hz, H-2); 4.91 (d, J = 10 Hz, H-20); 5.18 (d, J = 6 Hz, H-26); 5.22 (d, J = 10 Hz, H-29); 5.35 (s, H-9).

EXAMPLE 60

10-Desoxy-Δ$^{10,11}$-Δ$^{23,24}$-33-tert-butyldimethylsilyloxy-FR520

Formula I: R$_1$=OtBDMS; R$_2$, R$_5$ absent; R$_3$=Et; R$_4$+R$_6$=oxo; R$_7$=MeO; n=2; single bond in position 9,10; double bonds in positions 10,11 and 23,24

Process variant i), dehydration

A solution of 1 g 33-tert-butyldimethylsilyloxy-FR520 and 2 g 4-dimethylaminopyridine in 100 ml of acetonitrile is reacted with 0.5 ml of methanesulfonic acid chloride and the mixture is stirred at room temperature for 24 hours. Then the mixture is distributed between acetic acid ethyl ester and 1N aqueous hydrochloric acid solution, the organic phase is separated, washed with saturated aqueous sodium chloride solution, dried over sodium sulfate, filtered and concentrated under reduced pressure. The title compound is obtained as a colourless foamy resin from the residue using column chromatography over silicagel (eluant n-hexane/acetic acid ethyl ester 3:1):

$^1$H-NMR: 1.64 and 1.76 (s+s, CH$_3$-C-19, CH$_3$-C-28); 2.05 (s, CH$_3$-C-11); 6.22 (dd, J$_1$=1, J$_2$=15 Hz, H-23); 6.68 (J$_1$=8, J$_2$=15 Hz, H-24).

The starting material is obtained as follows: to a solution of 80 mg FR520 in 3 ml of dichloromethane are added 15 mg imidazole and 17 mg tert-butyldimethylsilyl chloride under stirring. The reaction mixture is stirred for 2 hours at room temperature, diluted with saturated aqueous ammonium chloride solution and extracted thrice with diethyl ether. The extract is washed with water and saturated sodium chloride solution, dried over sodium sulfate, concentrated under reduced pressure and chromatographically purified. 33-O-tert-butyldimethylsilyloxy-FR520 is obtained.

The compound of Example 31 may also be obtained in analogous manner according to process variant i).

EXAMPLE 61

21-Desallyl-21-cyclopropylmethyl-FK506

Formula I: $R_1, R_2 = OH$; $R_3 = $ cyclopropylmethyl; $R_4 + R_6 = $ oxo; $R_5 = OH$; $R_7 = MeO$; $n = 2$; single bonds in positions 9,10; 10,11 and 23,24

Process variant j), reaction with diazomethane or -ethane

A solution of 200 mg FK506 and 20 mg palladium(II) acetate in 5 ml of diethylether is cooled to $-5°$ and reacted dropwise with a 1M solution of diazomethane freshly prepared from N-nitrosomethylurea. The originally orange-coloured reaction mixture takes a light brown coloration after addition of 3 to 4 ml of diazomethane solution and a slight amount of a black precipitate forms. After addition of altogether 20 ml of diazomethane solution the reaction mixture is left at $-5°$ for 1 hour. The precipitate is filtered over silicium dioxide (Celite ®) and the solution concentrated under reduced pressure. The residue is purified by chromatography over silicagel using acetic acid ethyl ester/toluene 4:1 as the eluant. The title compound is obtained as a white amorphous solid:

$^1$H-NMR: S-cis/S-trans rotamers=5/2 0.0–0.12 (m, 2H,cyclopropyl); 0.35–0.47 (m, 2H, cyclopropyl); 0.57–0.71 (m, H, cyclopropyl).

Immunosuppressant activity may e.g. be determined in the following test methods:

4. Proliferative response of lymphocytes to allogen stimulation in the mixed lymphocyte reaction (MLR) in vitro: T. Meo, "The MLR in the Mouse", Immunological Methods, L. Lefkovits and B. Pernis, Eds., Academic Press, New York (1979), 227–239;

The compounds of the invention elicit in this test suppression of mixed lymphocytes at a dosage of from about 0.01 nM to about 10 nM.

5. Inhibition of the primary humoral immune response to sheep erythrocytes in vitro: R. I. Mishell and R. W. Dutton, Science 153 (1966) 1004–1006; R. I. Mishell and R. W. Dutton, J. Exp. Med. 126 (1967) 423–442.

The compounds are active in this test at a concentration of from about 0.5 nM to about 10 nM.

The compounds of the invention are therefore indicated as immunosuppressant and antiinflammatory agents for use in the prevention and treatment of conditions requiring immunosuppression and of inflammatory conditions, such as a) the prevention and treatment of
    resistance in situations of organ or tissue transplantation, e.g. of heart, kidney, liver, bone marrow and skin,
    graft-versus-host disease, such as following bone mar- The following compounds of formula I are obtained further in accordance with process variant j) in a manner analogous to Example 61:

| Example No. | $R_1$ | $R_2$ | $R_3$ | $R_4$ and config. at C-9** | $R_5$ | $R_6$ | $R_7$ | n | Bonds at positions 9,10 | 10,11 | 23,24 | Physicochemical characterization data |
|---|---|---|---|---|---|---|---|---|---|---|---|---|
| 62 | OAc | OH | cProme | =O with $R_6$ | OH |  | MeO | 2 | sb | sb | sb | acs; NMR* |
| 63 | OAc | OAc | cProme | =O with $R_6$ | OH |  | MeO | 2 | sb | sb | sb | acs; NMR* |
| 64 | OtBDMS | OtBDMS | cProme | OH (S) | OH | H | MeO | 2 | sb | sb | sb | acs; NMR* |
| 65*** | OH | OH | MecProme | =O with $R_6$ | OH |  | MeO | 2 | sb | sb | sb | acs NMR* |

*NMR: Example 62: $^1$H-NMR: 0.35–0.46 (m, 2 H, cyclopropyl); 0.58–0.72 (m, 1 H, cyclopropyl); 2.07 (s, OAc); 4.69 (m, H-33);
Example 63: $^1$H-NMR: 0.0–0.1 (m, 2 H, cyclopropyl); 0.35–0.45 (m, 2 H, cyclopropyl); 0.56–0.66 (m, 1 H, cyclopropyl); 2.07 (s) and 2.02 (s, —OAc); 4.68 (m, H-33);
Example 64: $^{13}$C-NMR: S-cis/S-trans rotamers = 3/1 Main product: 4.8 and 8.8 (cyclopropane); 99.6 (C-10); 123.2 (C-20); 130.8 (C-29); 134.1 (C-28); 139.9 (C-19); 169.6 (C-1); 173.4 (C-8); 210.2 (C-22); Side product: 4.2 and 8.9 (cyclopropane); 97.5 (C-10); 124.3 (C-20); 132.5 (C-28); 133.0 (C-29); 137.7 (C-19); 170.2 (C-1); 171.2 (C-8); 210.8 (C-22);
Example 65: $^1$H-NMR: −0.25 to −0.35 (m, 1 H, cyclopropyl); 0.26–0.10 (m, 1 H, cyclopropyl); 0.55–0.28 (m, 1H, cyclopropyl); 0.65–0.55 (m, 1 H, cyclopropyl);
**Insofar as C-9 is asymmetrically substituted;
***Approximately 3:1 mixture of the two cyclopropane diastereoisomers.
The compound of Example 33 may also be obtained analogously according to process variant j).

The compounds of the invention possess pharmacological activity. The are indicated for use as pharmaceuticals.

In particular they possess antiinflammatory and immunosuppressant activity.

Antiinflammatory activity may e.g. be determined in the following test methods:

1. Oxazolone allergic contact dermatitis in the mouse in vivo upon topical application: the test method is as described in e.g. EP 315978.

The compounds of the invention elicit in this test an activity between about 20% and about 75% upon topical administration at a concentration of 0.01%.

2. Inhibition of the oxidative burst in human neutrophil polymorphonuclear leukocytes (inhibition of the FMLP- or A23187-stimulated chemiluminescence) in vitro: the test method is as described in e.g. EP 315978.

3. Inhibition of macrophage activation [inhibition of TPA (12-O-tetradecanoylphorbol-13-acetate) induced release of $PGE_2$ (prostaglandin $E_2$) from mouse macrophages in vitro]: the test method is as described in e.g. EP 315978.

row grafts,
autoimmune diseases such as rheumatoid arthritis, systemic Lupus erythematosus, Hashimoto's thyroidis, multiple sclerosis, Myasthenia gravis, diabetes type I and uveitis,
cutaneous manifestations of immunologically-mediated illnesses;

b) the treatment of inflammatory and hyperproliferative skin diseases, such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and acne; and c) Alopecia areata.

The compounds may be administered systemically or topically.

For these indications the appropriate dosage will, of course, vary depending upon, for example, the host, the mode of administration and the nature and severity of the condition being treated. However, in general, satisfactory results are indicated to be obtained systemically at daily dosages of from about 0.15 mg/kg to about 1.5 mg/kg animal body weight. An indicated daily dosage is in the range from about 0.01 mg to about 100 mg, conveniently administered, for example, in divided doses up to four times a day or in retard form.

For topical use satisfactory results are obtained with local administration of a 1-3% concentration of active substance several times daily, e.g. 2 to 5 times daily. Examples of indicated galenical forms are lotions, gels and creams.

Preferred in the above indications are the following compounds of the invention:

9(R)-dihydro-10-desoxy-$\Delta^{10,11}$-FK506 (compound of Example 11);

33-acetoxy-9(S)-dihydro-FK506-9,10-carbonate (compound of Example 20);

33-pivaloyloxy-9(S)-dihydro-FR520 (compound of Example 25);

9(R)-dihydro-10-desoxy-$\Delta^{10,11}$-FR520 (compound of Example 30);

21-desallyl-21-cyclopropylmethyl-FK506 (compound of Example 61); and 21-desallyl-21-methylcyclopropylmethyl-FK506 (compound of Example 65).

The compounds of Examples 11, 20, 25, 30, 61 and 65 are the preferred compounds as immunosuppressant agents. It has, for example, been determined that in test 4. above these compounds have an $IC_{50}$ of respectively, less than 0.008; 0.006; 0.068; 0.023; less than 0.008; and 0.006 ug/ml, as compared to 0.002 ug/ml for cyclosporin A. It is, therefore, indicated that for this indication the compounds of Examples 11, 20, 25, 30, 61 and 65 may be administered to larger mammals, for example humans, by similar modes of administration at similar dosages than conventionally employed with cyclosporin A.

The compounds of the invention may be administered by any conventional route, in particular enterally, e.g. orally, e.g. in the form of tablets or capsules, or topically, e.g. in the form of lotions, gels or creams.

Pharmaceutical compositions comprising a compound of the invention in association with at least one pharmaceutical acceptable carrier or diluent may be manufactured in conventional manner by mixing with a pharmaceutically acceptable carrier or diluent. Unit dosage forms contain, for example, from about 0.0025 mg to about 50 mg of active substance.

Topical administration is e.g. to the skin. A further form of topical administration is to the eye, for the treatment of immune-mediated conditions of the eye, such as: auto-immune diseases, e.g. uveitis, keratoplasty and chronic keratitis; allergic conditions, e.g. vernal conjunctivitis; inflammatory conditions and corneal transplants, by the topical administration to the eye surface of a compound of the invention in a pharmaceutically acceptable ophthalmic vehicle.

The ophthalmic vehicle is such that the compound is maintained in contact with the ocular surface for a sufficient time period to allow the compound to penetrate the corneal and internal regions of the eye, e.g. the anterior chamber, posterior chamber, vitreous body, aqueous humor, vitreous humor, cornea, iris/ciliary, lens, choroid/retina and sclera.

The pharmaceutically acceptable ophthalmic vehicle may be e.g. an ointment, vegetable oil, or an encapsulating material.

We claim:

1. A compound of formula I

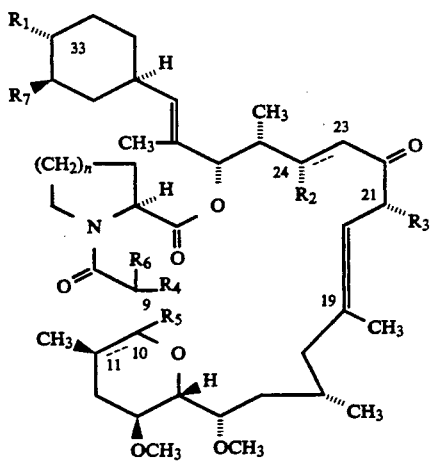

wherein $R_1$ is acyloxy or hydroxy or tert-butyldimethylsilyloxy;

$R_2$ is hydroxy or tert-butyldimethylsilyloxy or is absent, whereby when $R_3$ is cyclopropylmethyl or methylcyclopropylmethyl, $R_2$ additionally can be hydrogen;

$R_3$ is methyl, ethyl, n-propyl, allyl, cyclopropylmethyl or methylcyclopropylmethyl;

either $R_4$ is hydrogen, hydroxy or tert-butyldimethylsilyloxy, acyloxy or is absent; and $R_5$ is unprotected hydroxy, halogen of atomic number of from 9 to 53 or is absent; or $R_4$ and $R_5$ together form a group —OC(=O)O— or —OC(=S)O—; and $R_6$ is hydrogen or, when $R_4$ and $R_5$ together form a group —OC(=O)O—, is hydrogen or methoxy;

or $R_4$ and $R_6$ together from a group oxo; and $R_5$ is unprotected hydroxy or halogen of atomic number of from 9 to 53 or is absent;

$R_7$ is unprotected hydroxy or methoxy; and n is 1 or 2, where acyloxy is alkylcarbonyloxy of 2 to 8 carbon or benzoyloxy substituted by halogen of atomic number of from 9 to 53 and protected hydroxy is tert-butyldimethylsilyloxy; with the proviso that a) at least one of $R_1$, $R_2$, $R_4$ and $R_5$ is other than unprotected hydroxy;

b) when $R_4$ and $R_6$ together form a group oxo, then either $R_3$ is cyclopropylmethyl or methylcyclopropylmethy; or $R_5$ is halogen of atomic number of from 9 to 53 or is absent; and c) when $R_1$ is acyloxy, then either $R_4$ and $R_6$ are other than together a group oxo; or $R_4$ and $R_6$ together form a group oxo and $R_5$ is halogen of atomic number of from 9 to 53 or is absent.

2. A compound according to claim 1 of formula I wherein $R_1$ is acetoxy or hydroxy or tert-butyldimethylsilyloxy;

$R_2$ is hydroxy or tert-butyldimethylsilyloxy or is absent;

$R_3$ is methyl, ethyl, n-propyl or allyl; either $R_4$ is hydrogen, hydroxy or tert-butyldimethylsilyloxy, acetoxy or is absent; and $R_5$ is unprotected hydroxy or halogen of atomic number of from 9 to 53 or is absent; or $R_4$ and $R_5$ together form a group —OC(=O)O— or —OC(=S)O—; and $R_6$ is hydrogen or, when $R_4$ and $R_5$ together form a group —OC(=O)O—, is hydrogen or methoxy; or $R_4$ and $R_6$ together form a group oxo; and $R_5$ is unprotected hydroxy or halogen of atomic number of from 9 to 53 or is absent;

$R_7$ is methoxy; and n is 1 or 2, with the provisos that a) at least one of $R_1$, $R_2$, $R_4$ and $R_5$ is other than unprotected hydroxy;

b) when $R_4$ and $R_5$ together form a group oxo, then $R_5$ is halogen of atomic number of from 9 to 53 or is absent; and c) when $R_1$ is acetoxy, then either $R_4$ and $R_6$ are other than together a group oxo; or $R_4$ and $R_6$ together form a group oxo and $R_5$ is halogen of atomic number of from 9 to 53 or is absent.

3. A compound according to claim 1 of formula I wherein $R_1$ is acetoxy or hydroxy or tert-butyldimethylsilyloxy;

$R_2$ is hydrogen or hydroxy or tert-butyldimethylsilyloxy;

$R_3$ is cyclopropylmethyl or methylcyclopropylmethyl; either $R_4$ and $R_5$ are unprotected hydroxy; and $R_6$ is hydrogen; or $R_4$ and $R_6$ together form a group oxo; and $R_5$ is unprotected hydroxy;

$R_7$ is methoxy; and n is 2, with the provisos that a) at least one of $R_1$, $R_2$, $R_4$ and $R_5$ is other than unprotected hydroxy;

b) when $R_1$ is acetoxy, then $R_4$ and $R_5$ are other than together a group oxo.

4. A compound according to claim 1 of formula I wherein $R_1$ is alkylcarbonyloxy of altogether 2 to 6 carbon atoms, benzoyloxy monosubstituted by halogen of atomic number of from 9 to 53 or hydroxy optionally protected by tert-butyldimethylsilyl;

$R_2$ is hydroxy optionally protected by tert-butyldimethylsilyl or is absent;

$R_3$ is ethyl, allyl, cyclopropylmethyl or methylcyclopropylmethyl; either $R_4$ is hydrogen, unprotected hydroxy, acetoxy or is absent;

$R_5$ is unprotected hydroxy, halogen of atomic number of from 9 to 53 or is absent; or $R_4$ and $R_5$ together form a group —OC(=O)O— or —OC(=S)O—; and $R_6$ is hydrogen or, when $R_4$ and $R_5$ together form a group —OC(=O)O—, is hydrogen or methoxy; or $R_4$ and $R_6$ together form a group oxo; and $R_5$ is unprotected hydroxy, halogen of atomic number of from 9 to 53 or is absent;

$R_7$ is methoxy; and n is 2, with the provisos that a) at least one of $R_1$, $R_2$, $R_4$ and $R_5$ is other than unprotected hydroxy;

b) when $R_4$ and $R_6$ together form a group oxo, then either $R_3$ is cyclopropylmethyl or methylcyclopropylmethyl; or $R_5$ is halogen of atomic number of from 9 to 53 or is absent; and c) when $R_1$ is alkylcarbonyloxy or benzoyloxy as defined in this claim, then either $R_4$ and $R_6$ are other than together a group oxo; or $R_4$ and $R_6$ together form a group oxo and $R_5$ is halogen of atomic number of from 9 to 53 or is absent.

5. A compound of formula I according to claim 1 selected from

9(R)-dihydro-10-desoxy-$\Delta^{10,11}$-FK506 (compound of Example 11);

33-acetoxy-9(S)-dihydro-FK506-9,10-carbonate (compound of Example 20);

33-pivaloyloxy-9(S)-dihydro-FR520 (compound of Example 25);

9(R)-dihydro-10-desoxy-$\Delta^{10,11}$-FR520 (compound of Example 30);

21-desallyl-21-cyclopropylmethyl-FK506 (compound of Example 61); and 21-desallyl-21-methylcyclopropylmethyl-FK506 (compound of Example 65).

6. A pharmaceutical composition useful in inducing immunosuppression or treating inflammation comprising a therapeutically effective amount of a compound according to claim 1 and a pharmaceutically acceptable carrier therefor.

7. A method of inducing immunosupression or treating inflammation in a subject in need of said treatment, which comprises administering to the subject a therapeutically effective amount of a compound according to claim 1.

* * * * *